(12) United States Patent
Yoon et al.

(10) Patent No.: US 8,381,746 B2
(45) Date of Patent: Feb. 26, 2013

(54) SHOPPING CART AUTO WASHING SYSTEM

(75) Inventors: Hyeong Won Yoon, Gyeonggi-do (KR); Soo-Nam Jung, Gyeonggi-do (KR); Il-Jung Yoon, Gyeonggi-do (KR)

(73) Assignee: Woori Car Wash Co., Ltd., Incheon (KR)

( * ) Notice: Subject to any disclaimer, the term of this patent is extended or adjusted under 35 U.S.C. 154(b) by 700 days.

(21) Appl. No.: 12/597,062

(22) PCT Filed: Jul. 16, 2008

(86) PCT No.: PCT/KR2008/004160
§ 371 (c)(1),
(2), (4) Date: Oct. 22, 2009

(87) PCT Pub. No.: WO2009/011541
PCT Pub. Date: Jan. 22, 2009

(65) Prior Publication Data
US 2010/0122717 A1    May 20, 2010

(30) Foreign Application Priority Data
Jul. 18, 2007    (KR) .......................... 10-2007-0071761

(51) Int. Cl.
*B08B 3/04*    (2006.01)
(52) U.S. Cl. ...................................................... 134/123
(58) Field of Classification Search .................. 134/123, 134/137, 199, 201
See application file for complete search history.

(56) References Cited

U.S. PATENT DOCUMENTS
2006/0107486 A1* 5/2006 Andre .............................. 15/302
2008/0178412 A1* 7/2008 Kiter ............................ 15/309.2

* cited by examiner

*Primary Examiner* — Michael Barr
*Assistant Examiner* — David Cormier
(74) *Attorney, Agent, or Firm* — Rabin & Berdo, P.C.

(57) ABSTRACT

The shopping cart washing machine includes a cart transporting means (200) which continuously transports a cart in a forward direction, a high pressure washing water spraying means (300) which washes the cart by spraying high pressure washing water to a surface of the cart, a handle washing means (400) which washes a handle (4) of the cart by brushing upper and lower surfaces of the handle (4) of the cart, a cart outside surface washing unit (500) which washes the outside surface of a container part (1) of the cart by brushing the sides of the container part (1), a cart inside space washing means (600) which is disposed inside the container part (1) and removes dirt from the container part (1) by vertical vibrations, a rinsing means (700) which removes dirt remaining on the surface of the washed cart by spraying high pressure washing water again, and a drying means (800) which removes water droplets remaining on the surface of the washed cart using hot air.

17 Claims, 19 Drawing Sheets

(a)

(b)

(56) # SHOPPING CART AUTO WASHING SYSTEM

CROSS-REFERENCE TO RELATED APPLICATIONS

The present application claims priority under 35 U.S.C. 119 of Korean Patent Application No. 10-2007-0071761, filed on Jul. 18, 2007.

TECHNICAL FIELD

The present invention relates to a shopping cart washing machine, and more particularly, to a shopping cart washing machine, which can automatically perform washing processing including a loading process, a washing process, a drying process, and a piling process.

BACKGROUND ART

Generally, people use shopping carts when shopping in large shopping centers, such as Wallmart or grocery corners of departments in order to load and carry lots of things during shopping. Such a shopping cart comprises a container part 1 in the form of an iron net container for containing various things, casters 2 provided at the lower end of the container part 1 for allowing the container part 1 to move, and a handle 4, which facilitates direction change and movement of the cart.

Since the carts are convenient tools for shopping, the shopping carts are being used in almost large-scale shopping centers by a lot of people every day. Accordingly, the carts used by a lot of people easily get dirt due to dust and grocer dregs. Moreover, various kinds of bacteria and germs are likely to stick to handles of the carts through hands of people and thus the carts may become sources of germs.

In the past, there were no effective shopping cart washing machines. Although there has been a sterilizing apparatus for sterilizing shopping carts using steam, the apparatus is not useful because some portion of the cart, such as a handle which is made of synthetic resin is deformed during a sterilizing process due to weak heat resistance of the synthetic resin. There has been another washing machine which washes the cart by spraying washing water. However, this washing machine cannot be automatically controlled, and thus operators are needed to manually control the washing machine. Further, this washing machine has another problem in that the cart is likely to be turned upside down in the machine due to pressure of the sprayed washing water. Accordingly, with this washing machine, washing efficiency was low. Moreover, since a container part of a cart, which is a loading part, is formed in an iron net form, it was difficult to completely remove the dirt sticking to the container part only by the means of brushing. In particular, a handle part of the cart, which is the part that may be severely contaminated, is hardly washed.

DISCLOSURE OF INVENTION

Technical Problem

This invention is conceived in view of the above-mentioned problems and an object of the invention is to provide a shopping cart washing machine which can automatically perform washing processing including a loading process, a washing process, a drying process, and a piling process, can transport shopping carts during the washing processing without shaking of the carts, and can effectively wash the shopping carts even to handles and inside spaces of the container parts (loading parts) of the carts.

Objects and advantages of the invention will become more apparent, and be concretized with embodiments. The objects and advantages of the invention will be accomplished by means shown in claims and combination of the means.

Technical Solution

In order to accomplish the objects and advantages of the invention, there is provided a shopping cart washing machine including a cart transporting means which continuously transports a cart in a forward direction, a high pressure washing water spraying means which washes the cart by spraying high pressure washing water to a surface of the cart, a handle washing means which washes a handle of the cart by brushing upper and lower surfaces of the handle of the cart, a cart outside surface washing unit which washes an outside surface of a container part of the cart by brushing sides of the container part, a cart inside space washing means which is disposed inside the container part and removes dirt in the container part by vertical vibrations, a rinsing means which removes dirt remaining on the surface of the washed cart by spraying the high pressure washing water again, and a drying means which removes water droplets remaining on the surface of the washed cart using hot air.

It is preferable that the cart transporting means include a pair of left and right chains, each engaged with sprockets, a pair of upper plates which is coupled to upper portions of the chains, respectively for supporting left and right casters of the cart, respectively, and which is moved along the chains for transporting the cart in a horizontal direction, and an anti-shaking member which is coupled to the left and right chains, which is disposed to cross a gap between the left and right chains and to protrude from upper surfaces of the upper plates, and on which a horizontal bar of the cart is placed, for preventing the cart from shaking.

It is preferable that the anti-shaking means include a horizontal fixed shaft fixed to sides of the left and right chains at ends thereof, respectively, and a fixing member which extends from an upper surface of the horizontal fixed shaft for transporting the cart without shaking by holding the horizontal bar of the cart and which has a recess at a center portion thereof for receiving the horizontal bar of the cart therein so that the cart does not shake.

It is preferable that the high pressure washing water spraying means include a washing water pipe having a tunnel shape, through which washing water taken in by a pump and having high pressure passes, and a plurality of rotating nozzles which sprays high pressure washing water by rotating themselves at regular intervals in the washing water pipe.

It is preferable that the handle washing means include a first horizontal brush and a second horizontal brush arranged adjacent to one another in a vertical direction for brushing an upper surface and a lower surface of the handle of the cart, respectively, a brush arm which supports the first horizontal brush and the second horizontal brush in a rotatable manner while it is in a close contact with the first and second horizontal brushes and which has guide protrusions at both sides thereof, a first actuator which is constituted as a pneumatic cylinder and which actuates the brush arm having the guide protrusions and the horizontal brushes supported by the brush arm in a back-and-forth direction, and a guide rail in which the guide protrusions of the brush arm are inserted to guide motion of the first horizontal brush and the second brush moving in the back-and-forth direction, the motion being performed by the first actuator, and the brush arm and which allows the guide protrusions to slide therein.

It is preferable that the cart outside surface washing means include a first vertical brush and a second brush which erect at both sides of the cart and which rotate in order to brush side surfaces of the container part of the cart, in which shafts of the first vertical brush and the second vertical brush are coupled to a first upper bracket and an end portion of a second upper bracket at an upper portion and to a first lower bracket and an end portion of a second lower bracket at a lower portion in a rotatable manner, respectively, in which the first upper bracket and the first lower bracket are fixedly coupled to a first rotational shaft rotatably installed on the bottom of the cart transporting means, and the second upper bracket and the second lower bracket are fixedly coupled to a second rotational shaft rotatably installed on the bottom of the cart transporting means, in which the first rotational shaft and the second rotational shaft are provided with a first tension spring and a second tension spring, respectively so that the first vertical brush and the second vertical brush are returned to their original positions after washing the outside surfaces of the container part of the cart.

It is preferable that the cart inside space washing means include a vibrating brush which has a body having an external shape corresponding to an internal shape of the container part of the cart, and a plurality of brush hair attached to an outer surface of the body which has an empty space therein, the vibrating removing the dirt in the container part of the cart by vertically vibrating, and a brush driving unit coupled to an upper portion of the vibrating brush for making the vibrating brush vibrate in a vertical direction.

In the shopping cart washing machine, it is preferable that a horizontal bar is coupled to an upper portion of the brush driving unit in an insertion manner, a vertically actuating cylinder which is provided to a lower end portion of the horizontal bar actuates the vibrating brush and the brush driving unit along with the horizontal bar by moving the horizontal bar in a vertical direction, movable columns are installed to erect at both sides of the horizontal bar for guiding vertical-direction motion of the horizontal bar and can reciprocate in a cart transporting direction, and column moving cylinders are provided at the back of the columns for reciprocating the movable columns.

It is preferable that the brush driving unit include a housing, a decelerating motor fixed to an inside surface of a wall of the housing, a driving cam eccentrically rotating as the decelerating motor starts to drive, a driven cam which is located under the driving cam and linearly moves in a vertical direction by rotation of the driving cam, a rod extending downward from a lower portion of the driven cam, and a spring provided to surround an outer surface of the rod, in which the rod sequentially penetrates a lower plate of the housing and a barrier plate which horizontally spreads across the inside space of the vibrating brush in a horizontal direction, the rod has threads at an end portion thereof, and fixing nuts are coupled to an upper portion and a lower portion of the barrier plate for coupling the rod and the barrier plate to one another so that the rod and the barrier plate are simultaneously moved.

It is preferable that the shopping cart washing machine further include a cart loading unit located near a starting stage of the cart transporting means for pushing the carts being in a standby state for washing the carts one by one, in which the cart loading unit includes a first inclined surface extending from the ground surface to the starting stage of the cart transporting means and a pushing means for pushing the cart so that the cart moves along the first inclined surface.

It is preferable that the pushing means include a pair of left and right chains, each engaged with a first sprocket and a second sprocket and moving in a circulating manner, a decelerating motor connected to the first sprockets, and a pushing plate coupled to and disposed between the left and right chains for pushing the handle of the cart.

In the shopping cart washing machine, it is preferable that a first fixed shaft is arranged to be fixed to the left and right chains at both ends, the first fixed shaft is inserted into a hole of a first hollow member, a lower end portion of the first hollow member is provided with a fixing block, a pushing plate is coupled and fixed to a front portion of the fixing block by nuts and bolts, and a second fixed shaft is disposed at downstream side of the first fixed shaft in parallel with the first fixed shaft and fixed to the chains and prevents the pushing plate from pivoting in a backward direction.

It is preferable that the first inclined surface be provided with an anti-slipping means which prevents the cart from slipping down on the first inclined surface.

It is preferable that the anti-slipping means include a supporting plate which supports the back of the horizontal bar of the cart, a pivoting member which supports the supporting plate in a manner such that the supporting plate pivots only in a forward direction, a supporting block which prevents the pivoting member from pivoting in a backward direction, and a twisting spring which gives elastic force to the pivoting member so that the pivoting member is returned to its original position after pivoting in the forward direction.

It is preferable that the shopping cart washing machine further include a cart discharging unit, which discharges the washed cart and is provided at an end stage of the cart transporting means, in which the cart discharging unit includes a second inclined surface extending from the end stage of the cart transporting means to the ground surface, and a cart discharging means which pushes the cart to move along the second inclined surface and to be discharged outside the shopping cart washing machine.

It is preferable that the cart discharging means includes a pushing member coming into contact with a back surface of the handle of the cart and thus pushes the handle of the cart, and a second actuator which actuates the pushing member in a back-and-forth direction.

It is preferable that the shopping cart washing machine further include a pushing plate which is a plate member for pushing the cart while it is in direct contact with the back surface of the handle of the cart, and a pivoting plate which is a plate member connected to the second actuator so that the pivoting plate is moved by the second actuator and also moves and pivots the pushing plate in one direction.

Advantageous Effects

According to the invention which is described above, loading, washing, drying, discharging, and stacking of carts can be automatically performed, it is possible to transport the carts without shaking during the washing, and it is possible to effectively wash even handles of carts and inside spaces of container parts of carts. Accordingly, people can use clean shopping carts.

BEST MODE FOR CARRYING OUT THE INVENTION

The structure and operational relationship of elements of a shopping cart according to the invention will be described with reference to the accompanying drawings.

Figure 1:
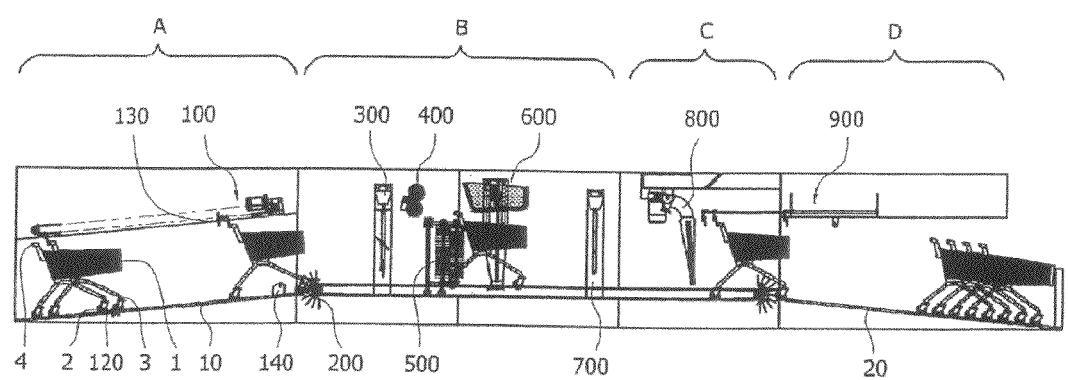
FIG. 1 is a side view illustrating a shopping cart washing machine according to the invention.
Figure 2:
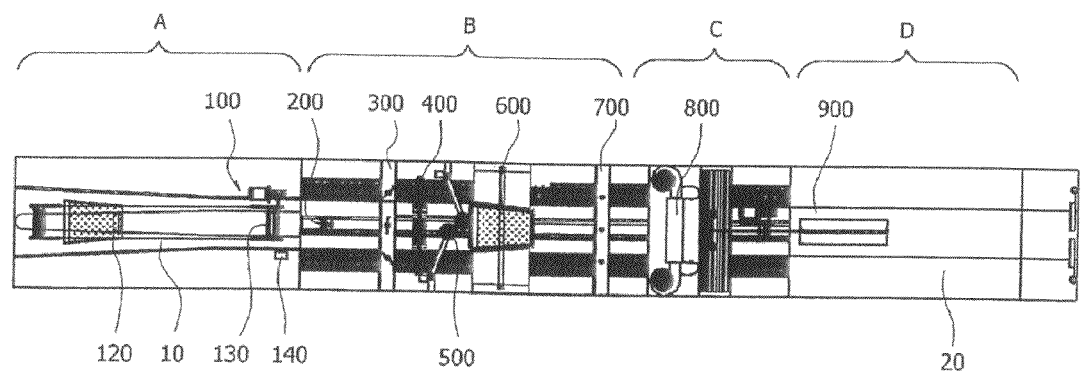
FIG. 2 is a plan view illustrating the shopping cart washing machine according to the invention.

FIG. 1 is a side view illustrating the entire structure of a shopping cart washing machine according to the invention, and FIG. 2 is a plan view illustrating the shopping cart washing machine according to the invention.

As shown in FIGS. 1 and 2, the shopping cart washing machine according to the invention includes a cart loading unit A, a cart washing unit B, a cart drying unit C, and a cart discharging unit D. A housing (not shown) of the shopping cart washing machine is made of transparent material so that the inside structure of the shopping cart washing machine is visible.

Figure 3:
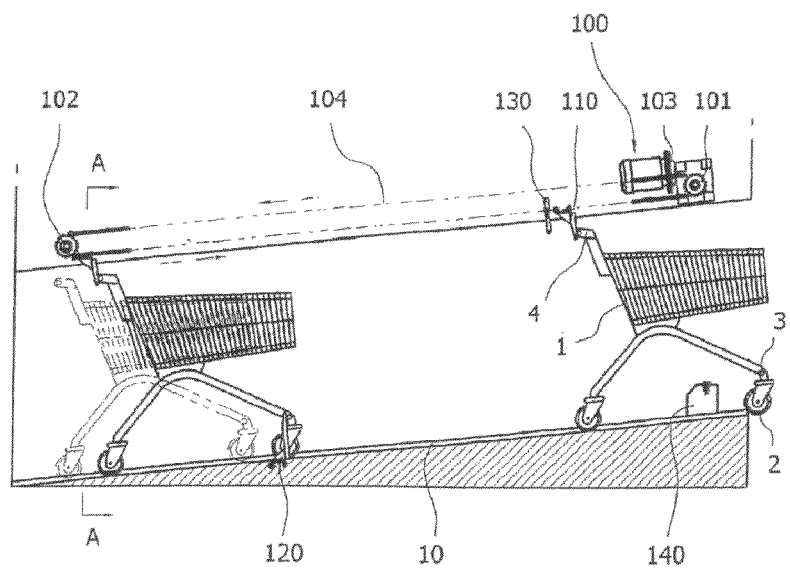
FIG. 3 is a side view illustrating a cart loading unit.

The cart loading unit A sequentially loads carts on the cart transporting unit 200 which sequentially passes through the cart washing unit B and the cart drying unit C one by one. The cart loading unit A includes a first inclined surface 10, a pushing means 100, and an anti-slipping means 120. FIG. 3 is a side view illustrating the side of the cart loading unit A.

As shown in FIG. 3, the first inclined surface 10 is a passage, through which a cart progresses toward the cart washing unit A. The cart washing unit A includes a space which stores water used in a washing process and in which the cart moves. Accordingly, it is preferable that the cart washing unit be located at a position higher than the surface of ground. For such a reason, the first inclined surface 10 needs to be installed on the passage, through which the cart is transported, i.e. between the ground surface and the cart washing unit A.

The first inclined surface 10 has a guide groove 12 extending in a lengthwise direction thereof. The guide groove 12 is formed at the center portion of the first inclined surface 10 and extends in the lengthwise direction of the first inclined surface so that the cart progresses and is introduced through entrance of the cart washing unit. As shown in FIG. 2, the width of the guide groove 12 is gradually decreased toward the upper end of the inclined surface 10 and thus right and left casters 2 of the cart are aligned with right and left sidewalls of the guide groove 12 at positions near the entrance of the cart washing unit. As a result, the cart is aligned as it comes closer to the entrance of the cart washing unit and is introduced into the cart washing unit in an aligned state.

The pushing means 100 pushes up the cart being standby for washing along the first inclined surface 10 to transport the cart toward the entrance of the cart washing unit A. Near the entrance of the cart washing machine, a plurality of used and stacked shopping carts is collected in a standby state. for washing. The pushing unit 100 sequentially introduces the shopping carts, which are piled, one by one into the cart washing unit A.

As shown in FIG. 3, the pushing means 100 includes left and right chains 104, each being engaged with a first sprocket 101 and a second sprocket 102 and moving in a circulating manner, decelerating motors 103 connected to the first sprockets 101, and a pushing plate 110 pivotably connected to the chains 104 in one direction for pushing the handle 4 of the cart.

With the above-mentioned structure, when the decelerating motor 103 starts to operate, the first and second sprockets 101 and 102 are rotated and the chains 104 move in one direction. Since the pushing plate 110 is connected to the chains 104 moving in one direction in a circulating manner, the pushing plate 119 comes to push the handle 4 of the cart.

Figure 4:
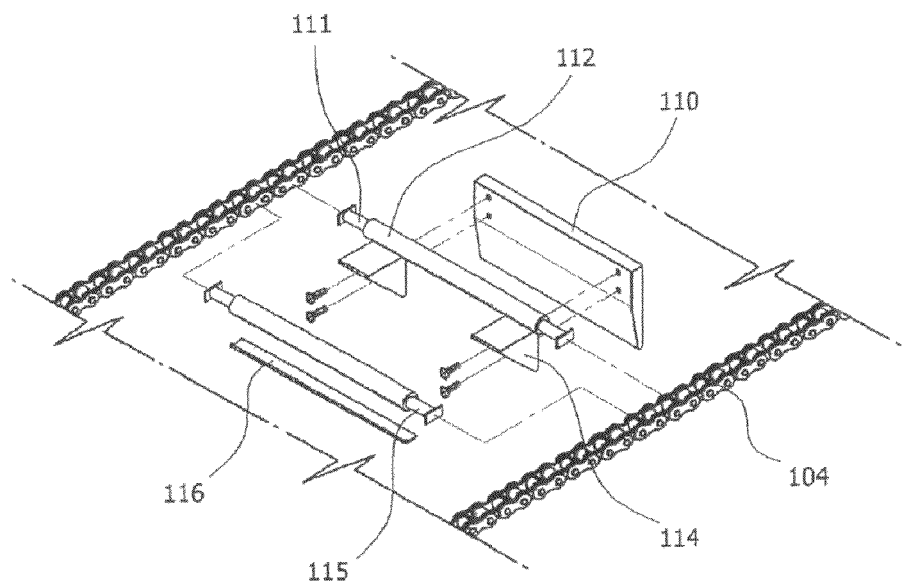
FIG. 4 is an exploded perspective view illustrating a posture in which a pushing plate is connected to chain.
Figure 5:
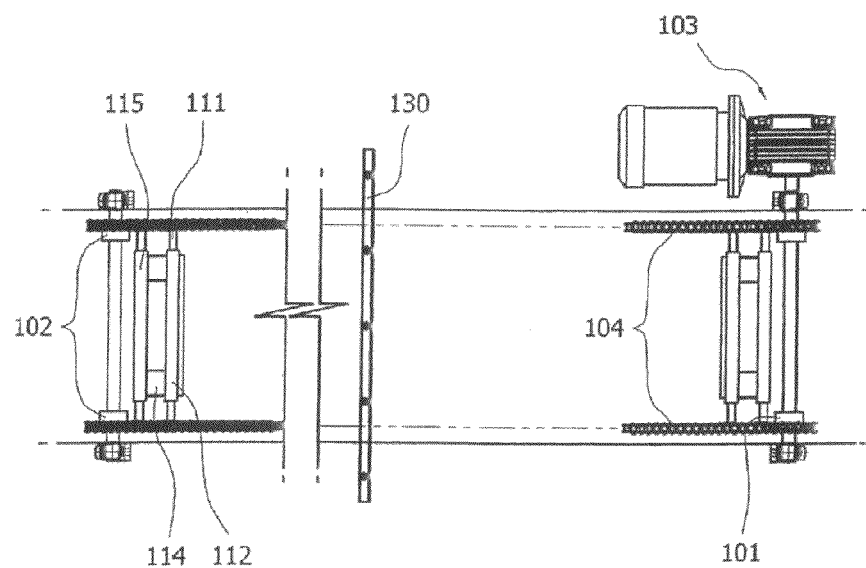
FIG. 5 is a plan view illustrating a coupling structure of the pushing plate and the chain.

FIG. 4 is an exploded perspective view illustrating the coupling structure between the pushing plate 110 and the chains 104, and FIG. 5 is a plan view illustrating the coupling structure between the pushing plate 110 and the chains 104.

As shown in FIG. 4, there is one pair of modules, each including the first sprocket 101, the second sprocket 102, and the chain 104, and the pushing plate 110 is located between left and right chains 104 of the two modules.

As shown in FIG. 4, a first fixed shaft 111 is located between the chains 104 to extend from the left chain 104 to the right chain 104 in a horizontal direction and is fixed through a welding process. The fixed shaft 111 is inserted in a hole of a first hollow member 112. A fixing block 114 is provided on the lower end of the first hollow member 112 and the pushing plate 110 is coupled and fixed to the fixing block 114 by threaded nuts and bolts.

At the downstream side of the first fixed shaft 111, a second fixed shaft 115 is located between and fixed to the right and left chains 104 to extend from the right chain to the left chain at both ends thereof. The second fixed shaft 115 serves as a stopper which prevents the pushing plate 110 from pivoting in a backward direction. That is, when pushing plate 110 pushes up the handle 4 of the cart, the first hollow member 112 is pivoted about the first fixed shaft 111. and the pushing plate 110 can pivot in the backward direction. In this manner, if the pushing plate 110 is pivoted in the backward direction, the pushing plate 110 cannot push up the handle 4 of the cart. Accordingly, in order to prevent such event from occurring, the second fixed shaft 115 serves as a stopper so that motion of the first hollow member 112 is interrupted by the upper surface of the fixing block 114 and thus the first hollow member 112 does not pivot on the first fixed shaft 111. At this time, in order to reduce the shock and prevent the damage from being caused attributable to the contact between the fixing block 114 and the second fixed shaft 115, a protective plate 116 may be additionally provided to a lower portion of the second fixed shaft 115.

Figure 6:
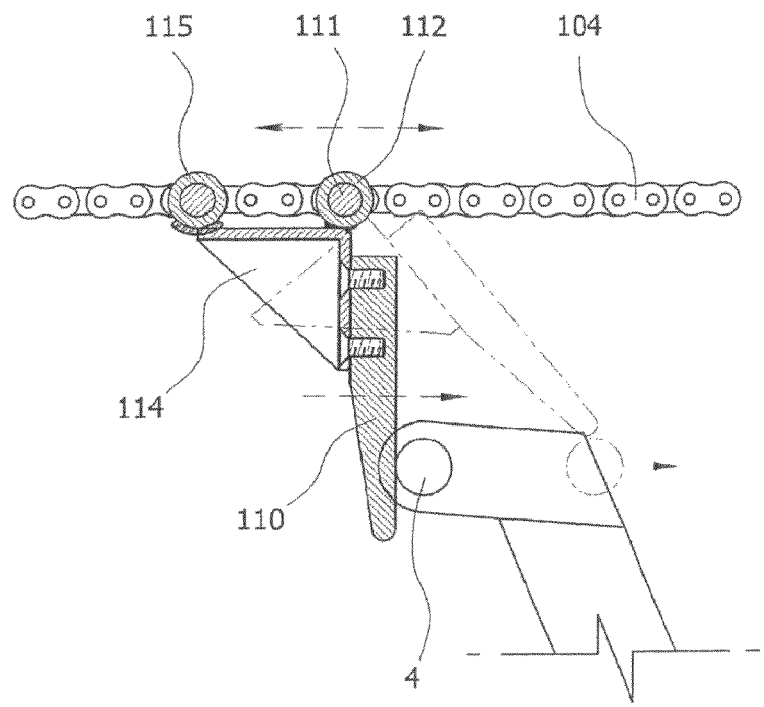
FIG. 6 is a view illustrating operation of the pushing plate.

FIG. 6 is a side view illustrating operation of the pushing plate 110. As shown in FIG. 6, when the chains 104 move, the pushing plate 110 coupled to the chains 104 progresses forward and finally is brought into contact with the handle 4 of the cart. When the pushing plate 110 comes into contact with the handle 4 of the cart, the pushing plate 10 pushes the handle 4 of the cart. At this time, the first hollow member 112 is relatively rotated about the first fixed shaft 111, and the pushing plate 110 and the fixing block 114 are applied with force exerting in a backward direction. At this time, since the upper surface of the fixing block 114 is brought into contact with the second fixed shaft 115, the pushing plate 115 is not rotated in the backward direction and thus can continuously push and transport the handle 4 of the cart.

The pushing plate 110 must introduce only a single cart into a main body of the cart washing unit at a single time. However, at an inappropriate timing, an error such that a plurality of carts progresses in a piled state may occur. In such an emergency situation, rotational direction of the decelerating motor 103 is changed in a reverse direction and thus the chains 104 come to move in an opposite direction. In this case, the pushing plate 110, as indicated by a two-dot chain line shown in FIG. 6, can rotate in the forward direction. Accordingly, the pushing plate 110 pivoted without interference with the handles 4 of the carts and thus can be returned to the original position.

Figure 7:
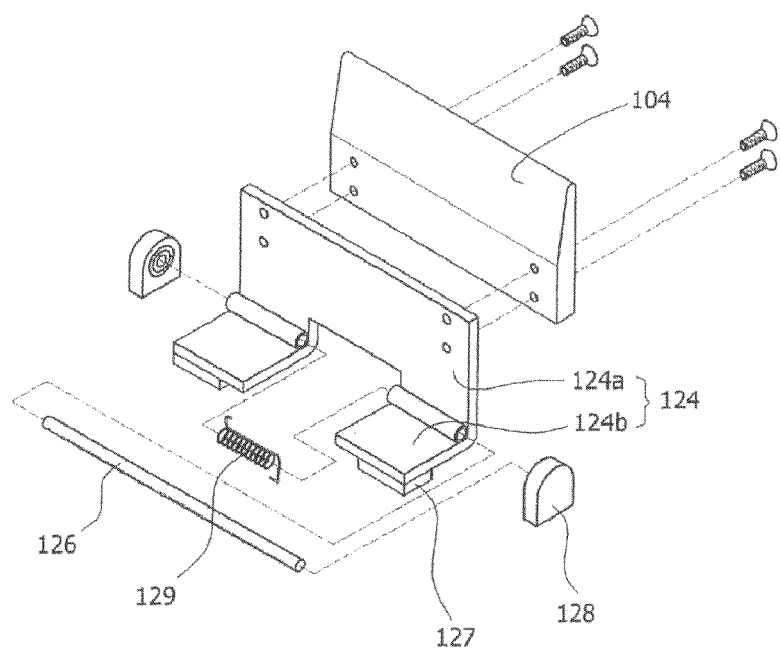
FIG. 7 is an exploded perspective view illustrating an anti-slipping means.

In addition, as shown in FIGS. 1 through 3, the first inclined surface 10 is provided with the anti-slipping means 120. The anti-slipping means functions to prevent the cart from being slipping back down along the first inclined surface 10 while the cart moves forward. FIG. 7 is an exploded perspective view illustrating the anti-slipping means 120. As shown in FIG. 7, the anti-slipping means 120 includes a supporting plate 122 and a pivoting member 124.

The supporting plate 122 supports a horizontal bar 3, which connects right and left legs of the cart to one another, from the back of the cart and thus prevents the cart from slipping down on the first inclined surface 10. As shown in FIG. 7, the supporting plate 122 is fixedly coupled to the pivoting member 124 by threaded nuts and bolts.

The pivoting member 124 is structured in a manner such that it pivots the supporting plate 122 in one direction. AS shown in FIG. 7, the pivoting member 120 has a shape in which it is bent so that vertical and horizontal parts 124a and 124b thereof are perpendicular to one another. A center portion of the horizontal part 124b and a center portion of part of the vertical part 124a are cut away.

Inside a bent portion of the pivoting member 124 is provided a second hollowed shaft 125. A shaft 126 is inserted in a hole of the second hollowed shaft 125 and the pivoting member 124 pivots on the shaft 126. Side supporting members 128 are coupled to external ends of the shaft 126 in an insertion manner and fixedly support the shaft 126. The side supporting members 128 are fixed to the first inclined surface 10. In addition, the outer circumferential surface of the shaft 126 extending across a cut portion at the center portion of the pivoting member 24 is provided with a twisting spring 129 and thus the pivoting member 124 is recovered to the original position by restoring force of the twisting spring 129 after the pivoting member 124 is pivoted. A lower end portion of the horizontal part 124b of the pivoting member 124 is provided with a supporting block 127 in order to prevent the pivoting member 124 from pivoting by being in contact with the first inclined surface 10.

Figure 8:
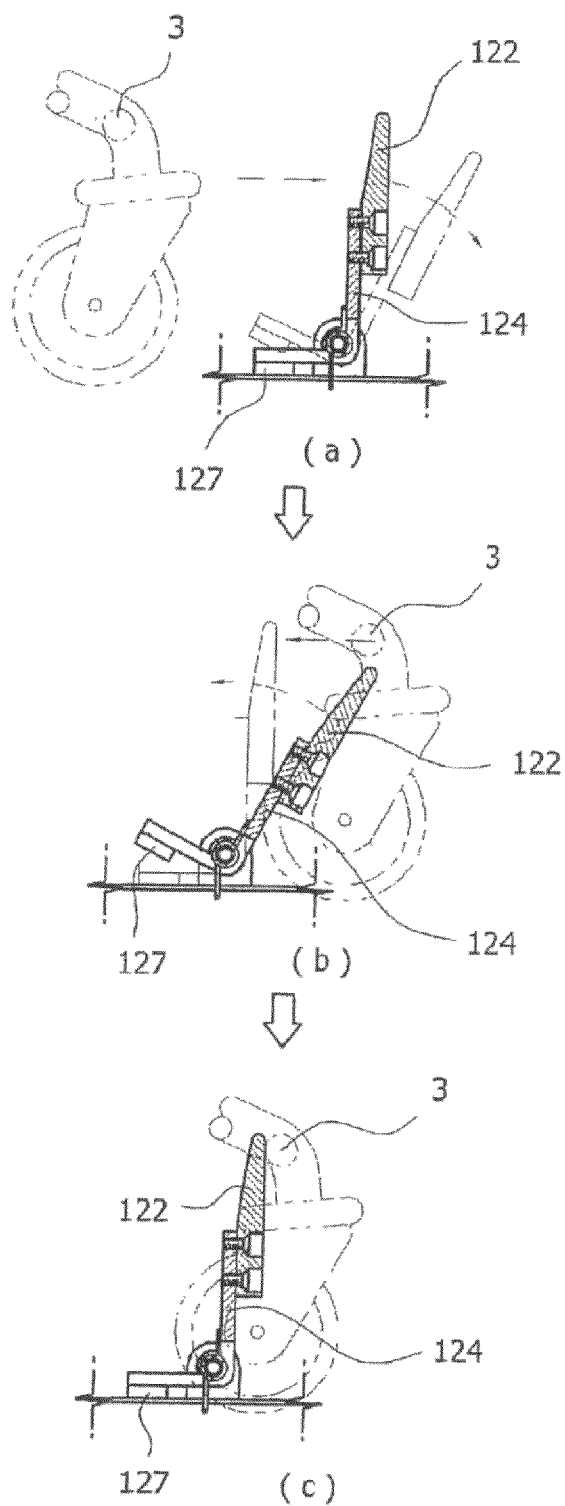
FIG. 8 is a side view illustrating operation of the anti-slipping means.

FIG. 8 is a side view illustrating operational relationship of elements of the anti-slipping means 120. As shown in FIG. 8, when the cart moves along the first inclined surface 10, if the horizontal bar 3 of the cart is brought into contact with the supporting plate 122, the supporting plate 122 is pivoted in the forward direction and the cart progresses. Then, the pivoting member 124 is returned to the original position by the restoring force of the twisting spring 120 provided to the pivoting member 124. As a result, the supporting plate 122 comes into contact with the back surface of the horizontal bar 3. As the supporting block 127 serves as the stopper on the first inclined surface 10, the pivoting member 124 is not pivoted any further. Accordingly, the supporting plate 122 supports the back of the horizontal bar 3 and thus can prevent the cart from slipping down.

Figure 9:
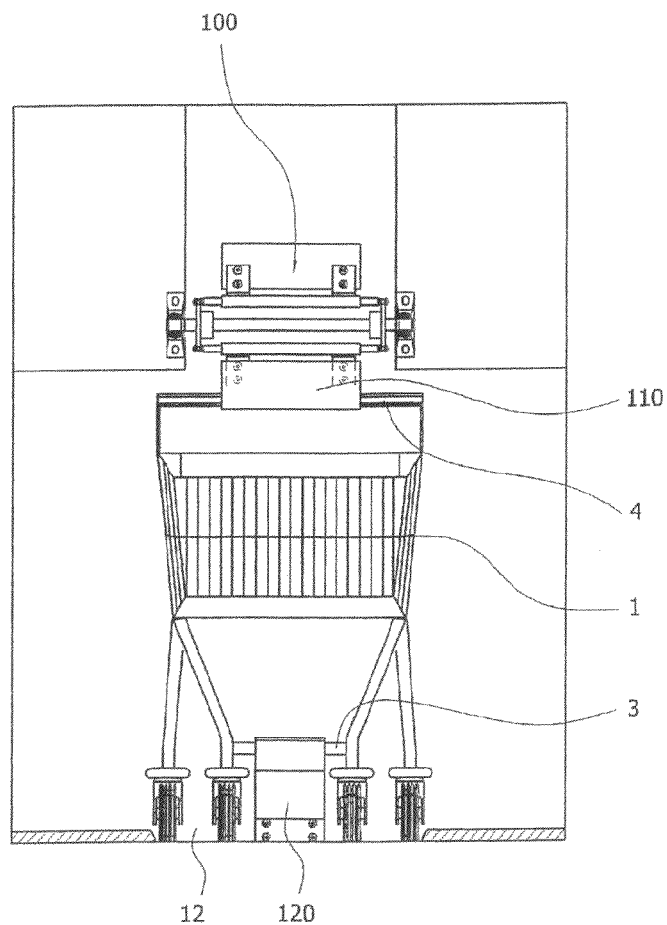
FIG. 9 is a rear view illustrating a posture in which the pushing means and the anti-slipping means push and support a cart.

FIG. 9 is a back view illustrating the state, in which the pushing means 100 pushes the cart and the anti-slipping means 120 supports the cart. As shown in FIG. 9, the handle 4 of the cart is pushed by the pushing plate 110, and the horizontal bar 3 is supported by the supporting plate 122. Accordingly, the cart can smoothly move along the first inclined surface 10.

In addition, as shown in FIG. 1 and FIG. 3, the first inclined surface 10 is provided with a position sensor 140 which checks whether there is any cart being standby for washing by detecting the front caster 2 of the cart introduced into the cart washing unit, and generates a signals for controlling stopping of operation of the decelerating motor which drives the chains to move, operation of various washing means provided in the cart washing unit, or operation of the drying means 800. The position sensor 140 is constituted as a proximity sensor or an optical sensor.

As shown in FIGS. 1, 3, and 5, the first inclined surface 10 is provided with a chemical spraying device 130, so that chemicals are sprayed to the carts being standby for washing and thus germs on the surface of the cart are removed.

Figure 10:
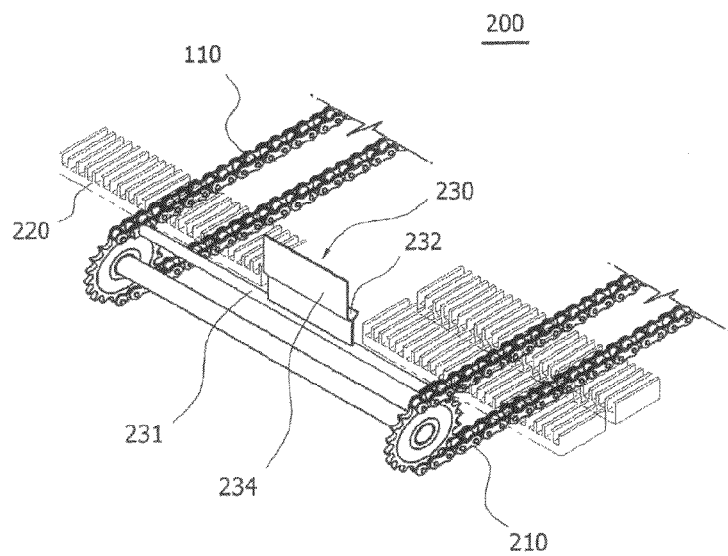
FIG. 10 is a view illustrating a can transporting means.

The cart transported along the first inclined surface 10 by the pushing means 100 in the cart loading unit A sequentially passes the cart washing unit B and the cart drying unit C. Thus, washing, rinsing, and drying processes are performed while the cart passes through the cart washing unit B and the cart drying unit C. The horizontal sequential movement of the cart is performed by the cart transporting means 200. FIG. 10 shows the cart transporting means 200 in detail. As shown in this drawing, the cart transporting means 200 includes chains 210, upper plates 220, and anti-shaking members 230.

Each of the chains 210 moves while it is engaged with the sprockets 201 and 202. There is one pair of left and right modules, each module including the chain 210 and the sprockets 201 and 202. The chains 210 are coupled to the upper plate 220 which supports the casters 2 of the cart, and transports the cart by continuously circulating. The surface of the upper plate 220 is provided with a plurality of grooves in which a plurality of protrusions protruding form the surface of the casters 2 is inserted. Accordingly, the cart is fixed to the upper plate 220 and it does not shake. The coupling structure of the chain 210 and the upper plate 220 is the same as the coupling structure of an upper plate 220 of a moving work in a large shopping center and casters 2. Accordingly, details of the coupling structure will be omitted. As shown in FIG. 10, the upper plate 220 is split into left and right parts and the left and right parts are coupled to the left and right chains respectively and left and right casters are placed on the left and right parts of the upper plate 220.

The anti-shaking member 230 is provided between the left and right chains 210. The anti-shaking member 230 is a member for fixing the cart in order to prevent the cart from turning upside down or shaking by high pressure washing water and brushes the cart while the cart is supported on the upper plate 220 and is moved on the upper plate 220 during the washing process. As shown in FIG. 10, the anti-shaking member 230 includes a horizontal fixed shaft 231 and a fixing member 234.

The horizontal fixed shaft 231 is disposed between the chains to extend from one chain to another and is fixed to the chains 210. The fixing member 234 is fixedly coupled to an upper surface of the horizontal fixed shaft 231 through a welding process. As shown in FIG. 10, it is preferable that the fixing member 234 extends from the upper surface of the horizontal fixed shaft 231 and has a recess 232 at a center portion thereof so that the horizontal bar 3 of the cart is received in the recess 232. As a result, the fixing member 234 holds the horizontal bar 3 of the cart by the recess 232 and thus it is possible to transport the cart without shaking. The fixing member 234 has any form as long as it has the recess 232 so that it holds the horizontal bar 3 of the cart and thus the cart is transported without shaking. With this structure, as the chains 210 circulate, the fixing member 234 connected to the chains 210 via the horizontal fixed shaft 231 is transported in a horizontal direction, and the horizontal bar 3 of the cart is received in the recess 232. Accordingly, the cart does not shake while it is transported.

Figure 11:
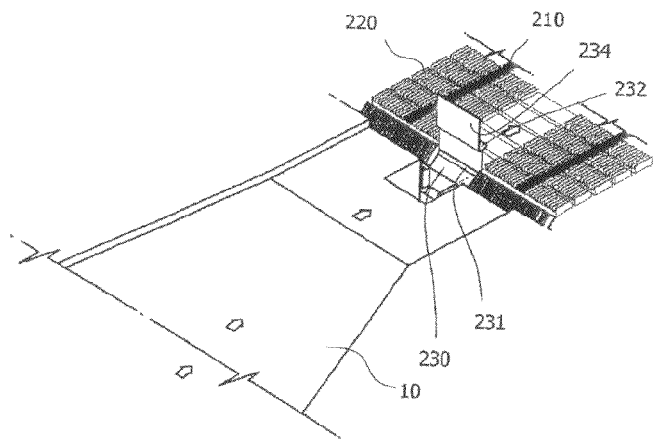
FIG. 11 is a perspective view illustrating a coupling structure of the cart transporting means and the cart loading unit.

FIG. 11 is a perspective view illustrating a coupling portion between the cart transporting means 200 and the cart loading unit. As shown in FIG. 11, the uppermost portion of the first inclined surface 10 of the cart loading unit includes a flat portion. A center portion below the flat portion of the first inclined surface 10 is cut and the fixing member 234 of the anti-shaking member 230 can pass through the cut portion of the first inclined surface 10. The casters 2 of the cart are supported by the left and right upper plates 220 of the anti-shaking member 230.

Figure 12:
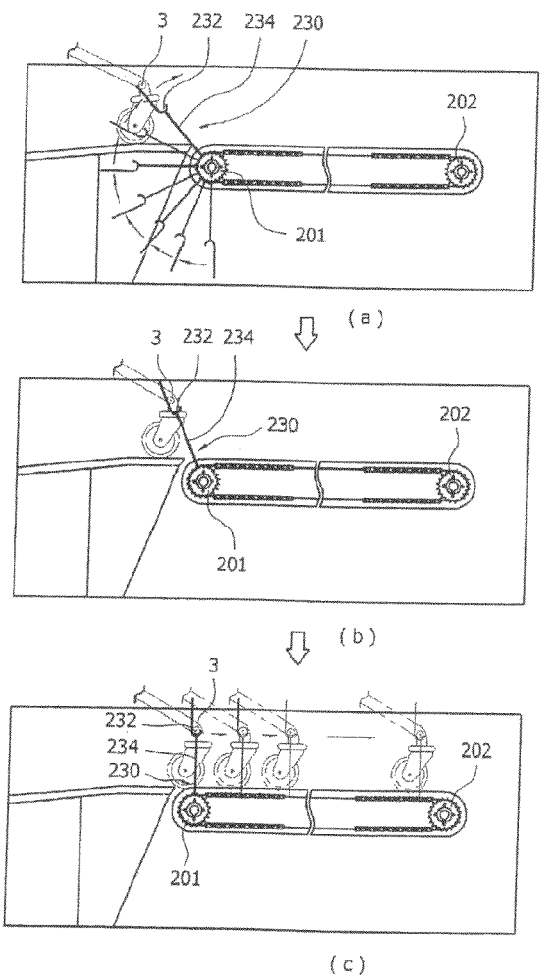
FIG. 12 is a schematic view illustrating a method in which an anti-shaking member holds the cart at an initial state of a cart washing unit and transports the cart.

FIGS. 12(*a*), 12(*b*) and 12(*c*) show a method that the anti-shaking member 230 holds and transports the cart near a starting stage. of the cart washing unit. As shown in the drawings, when the cart reaches the entrance of the cart washing unit first, the fixing member 234 of the anti-shaking member 230 comes to rotate along circulation of the chains 210 and is transported from a lower portion to an upper portion. An end of the fixing member 234 comes into contact with the back surface of the horizontal bar 3 of the cart. As the chains continuously circulate, the fixing member 234 rotates and thus pushes the horizontal bar 3 of the cart. In this manner, the fixing member 234 rotates and thus pushes the horizontal bar 3 of the cart. When the fixing member 234 comes to erect,
the horizontal bar 3 is stably placed in the recess 232 of the fixing member 234. Next, the chains 210 are separated from the sprockets and circulate in a horizontal direction. Accordingly, the fixing member 234 holds the horizontal bar 3 of the cart while it is erected and is moved in a horizontal direction. Accordingly, the cart is stably transported along the cart transporting means 200 without shaking. In short words, the cart sequentially passes through the cart washing unit and the cart drying unit while it moves along the cart transporting means 200.

The cart, which is transported along the first inclined surface 10 by the cart loading unit, is washed using high pressure washing water and brushes, and then rinsed. As shown in FIG. 1, the cart washing unit includes a high pressure washing water spraying means 300, a handle washing means 400, a cart outside surface washing means 500, a cart inside space washing means 600, and a rinsing means 700.

Figure 13:
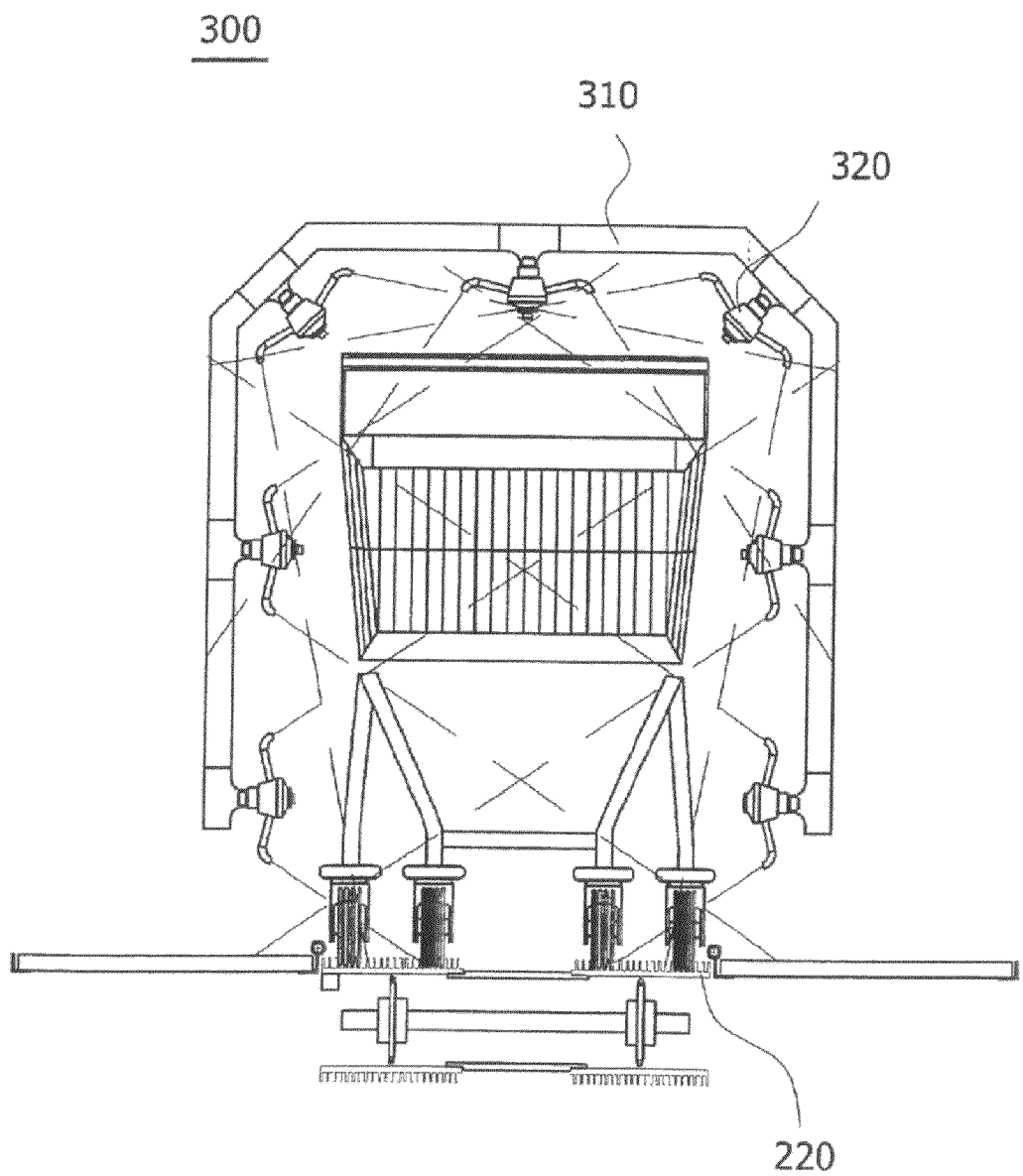
FIG. 13 is a schematic view illustrating a posture in which the cart is washed by a high pressure washing means.

The high pressure washing water spraying means 300 primarily removes dirt sticking to the cart by spraying high pressure washing water to the cart. FIG. 13 shows that the cart is being washed by the high pressure washing water spraying means, and FIG. 14 shows the overall structure of the high pressure washing means.

Figure 14:
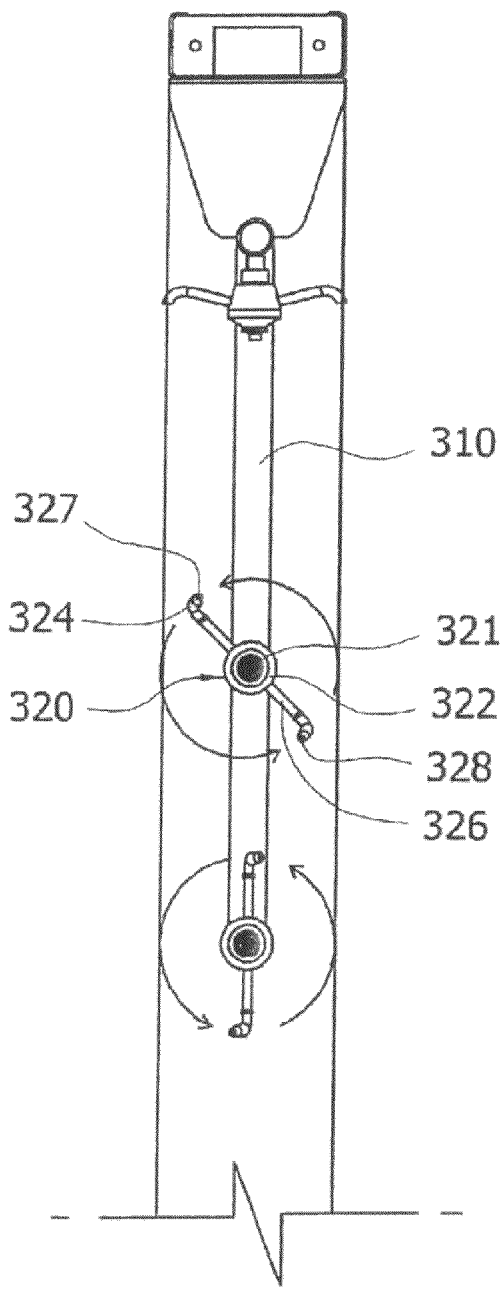
FIG. 14 is a view illustrating the overall structure of the high pressure washing means.

As shown in FIGS. 13 and 14, a washing water pipe 310, through which water, taken in by a pump and having high pressure, flows, is installed on the inside surface of a wall of the housing. The washing water pipe 310 has a tunnel form so that washing water is effectively sprayed in all directions to the cart. A plurality of rotating nozzles 320, which sprays high pressure washing water at regular intervals while rotating themselves, is installed in the washing water pipe 310.

As shown in FIG. 14, the rotating nozzle 320 includes a rotating body 322, which is rotatable about a central shaft 321, and a first spraying nozzle 324 and a second spraying nozzle 326, which protrude from the rotating body 322 in opposite directions. Ends of the first spraying nozzle 324 and the second spraying nozzle 326 are provided with a first spraying hole 327 and a second spraying hole 328, respectively. Through the first and second spraying holes 327 and 328, high pressure washing water is sprayed. Since the first and second spraying holes 327 and 328 are bent at an angle so as to direct in opposite directions, in the case in which high pressure washing water is sprayed through the first and second spraying holes 327 and 328, the rotating body 322 rotates about the central shaft 321 by spraying pressure. As the nozzles rotate themselves when the high pressure washing water is sprayed, it is possible to wash the entire body of the cart with the decreased number of nozzles in comparison with the case in which fixed nozzles are used and it is possible to eliminate a dead space for washing.

Figure 15:
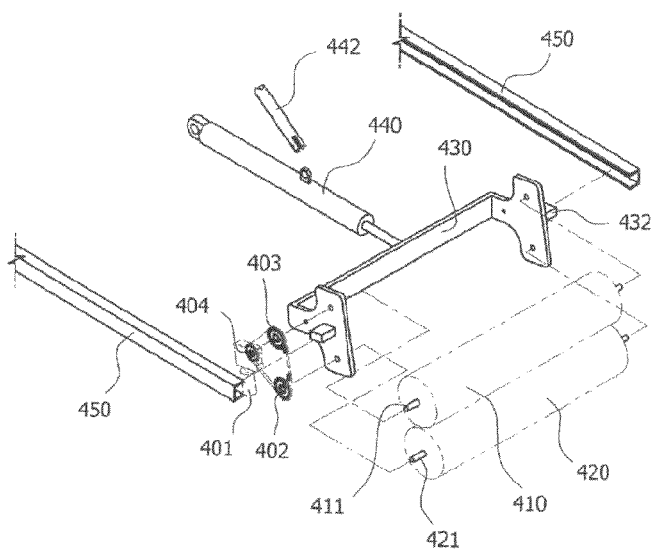
FIG. 15 is an exploded perspective view illustrating a handle washing means.

The cart, which is primarily washed by high pressure washing water by the high pressure spraying means 300, is washed using brushes in a next step. With reference to FIG. 1, the handle 4 of the cart is washed by the handle washing means 400. FIG. 15 is an exploded perspective view illustrating the handle washing means 400 and FIG. 16(*a*) and FIG. 16(*b*) are side views illustrating a method of washing the handle 4 using the handle washing means 400.

Figure 16:
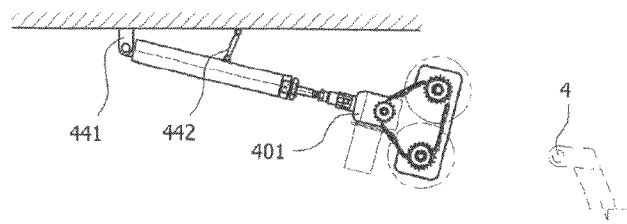
FIGS. 16(a) and 16(b) are side views illustrating a method of washing a handle of the can by the handle washing means.
Figure 16:
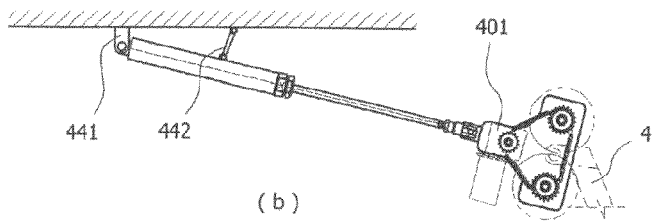

As shown in FIGS. 15, 16(*a*) and 16(*b*), the handle washing means 401) includes a first horizontal brush 410, a second horizontal brush 420, a brush arm 430, and a first actuator 440.

The first and second horizontal brushes 410 and 440 are brushes arranged adjacent to one another in a vertical direction. The first horizontal brush 410 brushes and washes the upper surface of the handle 4 of the cart, and the second horizontal brush 420 brushes the lower surface of the handle 4. Brush shafts 411 and 421 of the first horizontal brush 410 and the second horizontal brush 420 are connected to sprockets 402 and 402 disposed at sides thereof and engaged with the decelerating motor 401. The sprockets 402 and 403 are connected to the decelerating motor 401 by a belt and rotate in endless manner. Accordingly, the first and second horizontal brushes 410 and 420 rotate and thus brush the surface of the handle.

In order to insert the handle 4 of the cart into a gap between the fust and second horizontal brushes 410 and 420 and wash the handle 4 of the cart, the first and second horizontal brushes 410 and 420 move along the cart progressing in a forward direction to wash the cart, and then must be returned to its original position for a next washing process after performing washing once. Such operation must be repeatedly performed. In order to perform such operation, the brush arms 430 and the first actuator 440 are used in order to hold and move the first and second horizontal brushes 410 and 420.

The brush arm 430 is a supporting member which rotatably supports the first and second horizontal brushes 410 and 420 which are adjacent in a vertical direction. The brush arm 430 has a U-shaped form. That is, it extends horizontally having a length corresponding to the first and second horizontal brushes 410 and 420, and is then bent at a right angle so that the brush shafts 411 and 421 are rotatably inserted. The decelerating motor 401 and the sprockets 402 and 403 are located at a side of the brush arm 430 and connected to the brushes 411 and 420 which penetrate the side of the brush arm 430.

The first actuator 400 is connected to a center portion of the brush arm 430. The first actuator 440 is constituted as a pneumatic cylinder and actuates the brush arm 430 and the horizontal brushes supported by the brush arm 430 in a forward direction and a backward direction. As shown in FIGS. 16(a) and 16(b), the first actuator 440 is installed at a ceiling portion of the housing by a first link 441.

In order to guide stable movement of the first and second horizontal brushes 410 and 420, moved forward and backward by the first actuator 440, and the brush arm 430 which supports the first and second horizontal brushes 410 and 420, as shown in FIG. 15, a guide rail 450 is provided on the inside wall of the housing. Sides of the brush arm 430 are provided with guide protrusions 432 sliding along the guide rail 450. With such a structure, the first horizontal brush 410 and the second horizontal brush 420 stably and precisely move toward the handle 4 of the cart and thus it is possible to effectively wash the handle of the cart.

As shown in FIG. 16(a), the first actuator 440 is in a contracted state. When the cart progresses and the handle 4 of the cart is located at the front of the handle washing means 400, as shown in FIG. 16(b), the first actuator expands. As a result, it pushes the brush arm 430 forwards. In this instance, the first and second horizontal brushes 410 and 420 move forward and the handle 4 of the cart is inserted between the first and second horizontal brushes 410 and 420. At this time, as the decelerating motor 401 rotates, the first and second horizontal brushes 410 and 420 are rotated and thus the upper and lower surfaces of the handle 4 of the cart are brushed. After finishing the brushing, the first actuator 440 is returned to the initial state, and is standby for a next washing.

Figure 17:
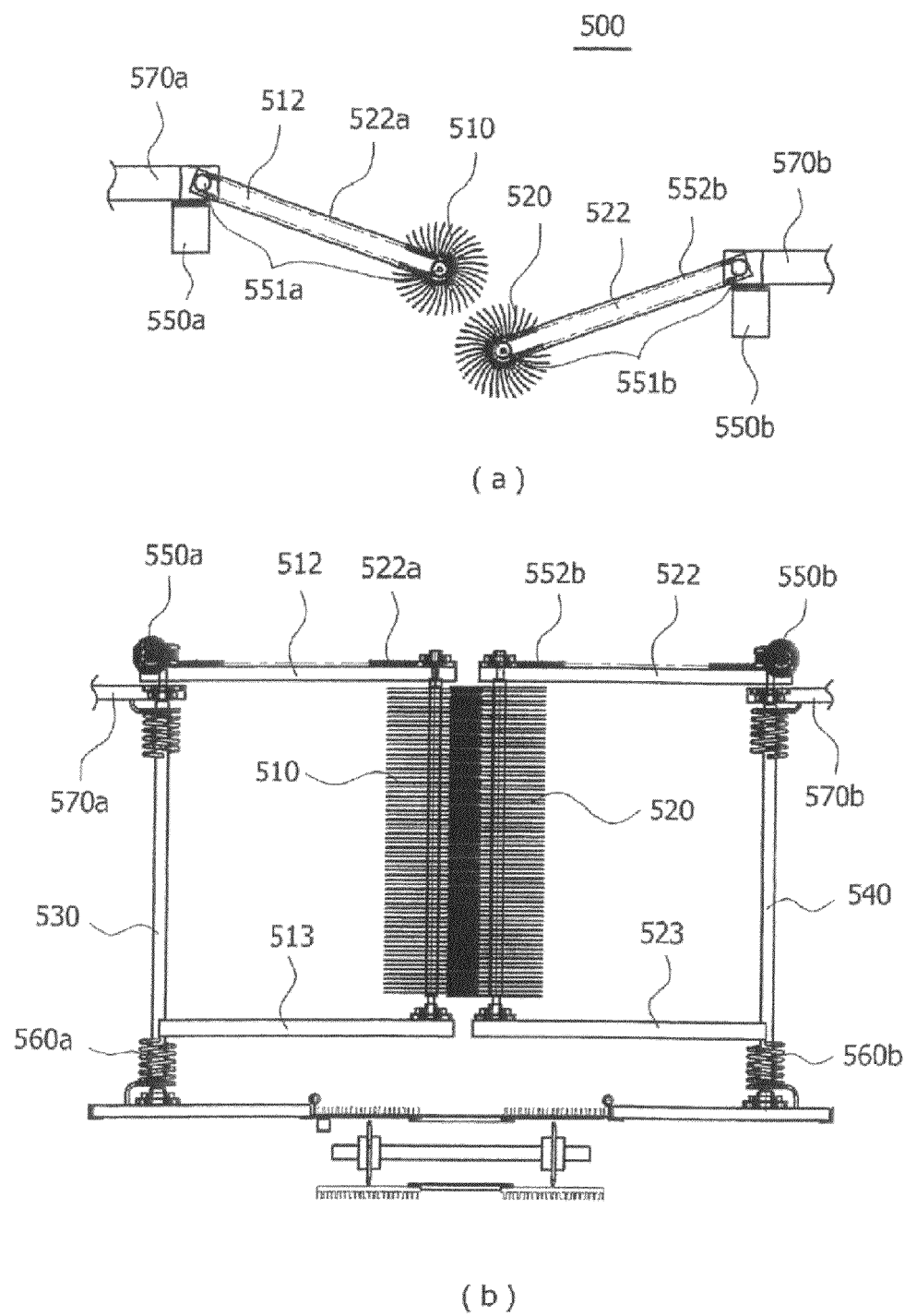
FIG. 17(a) is a plan view illustrating a cart outside surface washing means.
FIG. 17(b) is a front view illustrating the cart outside surface washing means.
Figure 18:
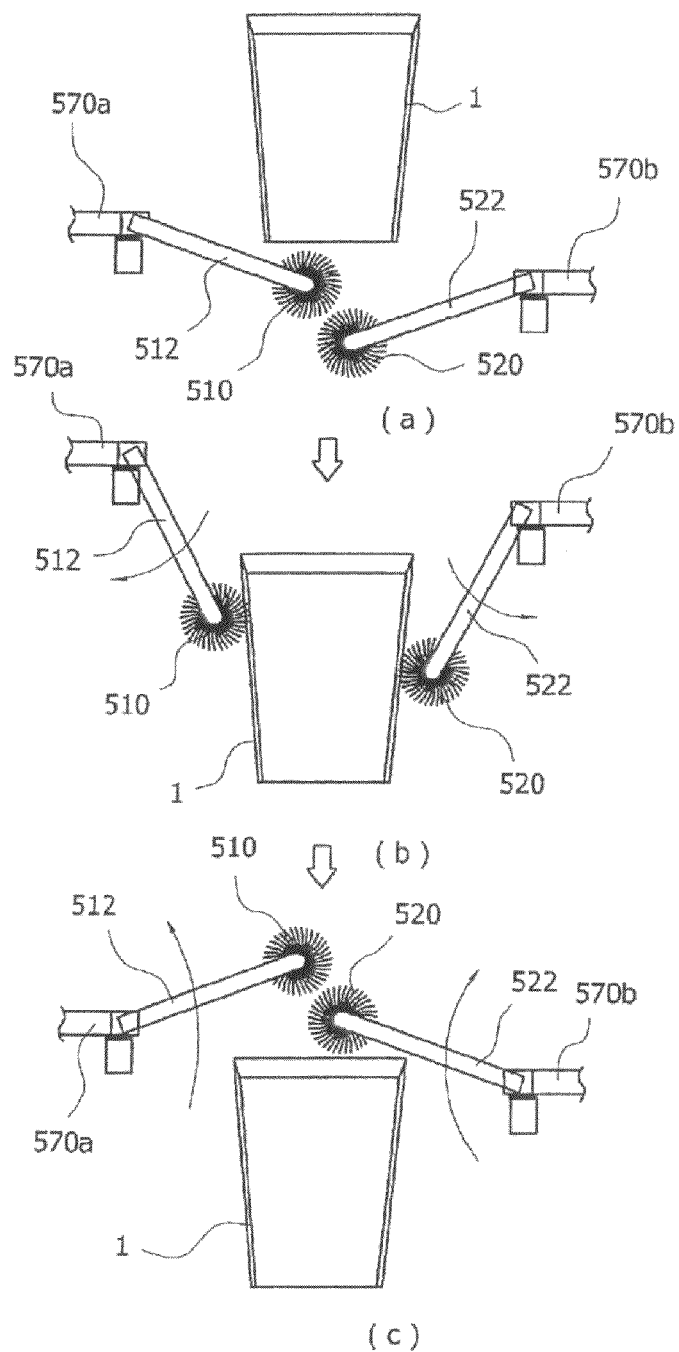
FIGS. 18(a), 18(b), and 18(c) are views illustrating a posture in which a container part of the cart is washed by the cart outside surface washing means.

The front portion of the handle washing means 400 is provided with a cart outside surface washing means 500. The cart outside surface washing means 500 is a portion for brushing the outer surface of the container part 1 of the cart. FIG. 17(a) is a plan view illustrating the cart outside surface washing means 500, and FIG. 17(b) is a front view illustrating the cart outside surface washing means 500. FIGS. 18(a), 18(b) and 18(c) schematically show operation of washing the outside surface of the container part 1 of the cart using the cart outside surface. washing means 500.

The cart outside surface washing means 500 washes the outside surface of the container part 1 of the cart by rotation of first and second vertical brushes 510 and 520 installed at left and right sides of the cart in a cart moving direction.

The first and second vertical brushes 510 and 520 are structured to rotate in erecting state. For such a structure, shafts of the first and second vertical brushes 510 and 520 are rotatably coupled to end portions of a first upper bracket 512 and a second upper bracket 522 at upper portions, and to end portions of a first lower bracket 513 and a second lower bracket 523 at lower portions, respectively. The first upper bracket 512 and the first lower bracket 513, and the second upper bracket 522 and the second lower bracket 523 are fixedly coupled to a first rotating shaft 530 and a second rotating shaft 540 rotatably installed on the bottom of the housing, and more particularly on the bottom of the cart transporting means 200, as shown in FIG. 17(b).

The first and second vertical brushes 510 and 520 rotate themselves and thus wash the outer surface of the container part 1 of the cart. The rotating structure of the vertical brushes may be a structure employed in conventional automatic car washing machines. However, with embodiments of the invention, the rotating structure of the vertical brushes includes the decelerating motors 550a and 550b, sprockets 551a and 551b, and chains 552a and 552b. As shown in FIGS. 17(a) and 17(b), shafts of the first and second vertical brushes 510 and 520 penetrate through the first and second brackets 512 and 522, respectively, and the sprockets are coupled to protruding portions of the shafts of the first and second vertical brushes 510 and 520. Remaining ends of the first and second upper brackets 512 and 522 are connected to the decelerating motors, and sprockets are rotated by rotation of the decelerating motors. The sprockets are connected to the decelerating motors by the chains and thus the first and second vertical brushes 510 and 520 are rotated by rotation of the decelerating motors.

With such a structure, washing is performed as the first and second vertical brushes 510 and 520 brush the outer surface of the container part 1 of the cart. FIGS. 18(a), 18(b) and 18(c) sequentially show the cart washing operation. As shown in FIG. 18(a), when the cart reaches the cart outside surface washing means 500, the front face of the container part 1 of the cart progresses while pushing the first and second vertical brushes 510 and 520 forwards. As shown in FIG. 18(b). as the first rotating shaft 530 and the second rotating shaft 540 are rotated, a couple of the first upper bracket 512 and the first lower bracket 513, a couple of the second upper bracket 522 and the second lower bracket 523, and a pair of the first vertical brush 510 and the second vertical brush 520 are rotated in the forward direction, and thus the first vertical and second vertical brushes 510 and 520 come to wash the outside surface of the container part 1 of the cart. If the cart continuously progresses, the first and second vertical brushes 510 and 520 are returned to the original positions, as shown in FIG. 18(c), and are standby for a next cart washing process.

As described above, after washing of the outside surface of the container part 1 of the cart is finished, the first and second vertical brushes 510 and 520 must be returned to the original positions. In order to embody such mechanism, as shown in FIG. 17(b), the first rotating shaft 530 and the second rotating shaft 540 are provided with a first tension spring 560a and a second tension spring 560b, respectively. The first and second tension springs 560a and 560b are wound around the first and second rotating shafts 530 and 540, respectively, first ends of the first and second tension springs are fixed to the bottom of the housing, and second ends of the first and second tension springs are fixed to the first and second rotating shafts 530 and 540, respectively. or to the first and second lower brackets 513 and 523, respectively. Upper portions of the first and second rotating shafts 530 and 540 are provided with additional first and second fixed brackets 570*a* and 570*b*, respectively, and tension springs. Thanks to the restoring force of the tension springs, the first and second vertical brushes 510 and 520 can be returned to the original positions after washing.

Figure 19:
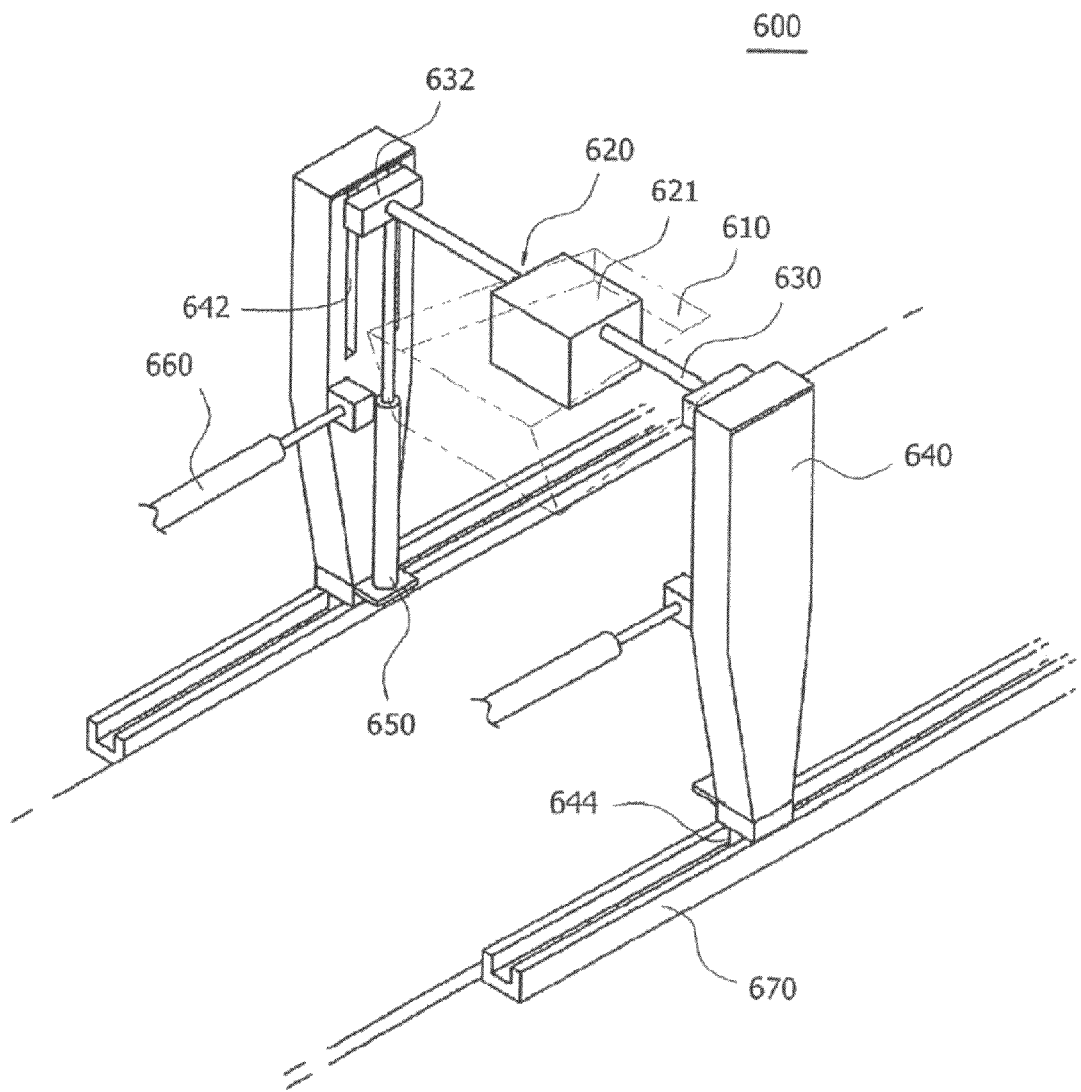
FIG. 19 is a perspective view illustrating a cart inside space washing means.
Figure 20:
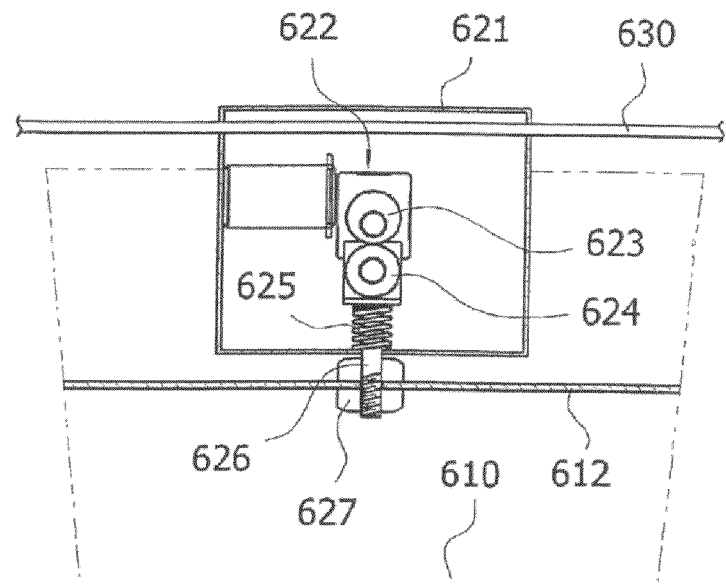
FIGS. 20(a) and 20(b) are cross-sectional views illustrating main part of the cart inside space washing means.
Figure 20:
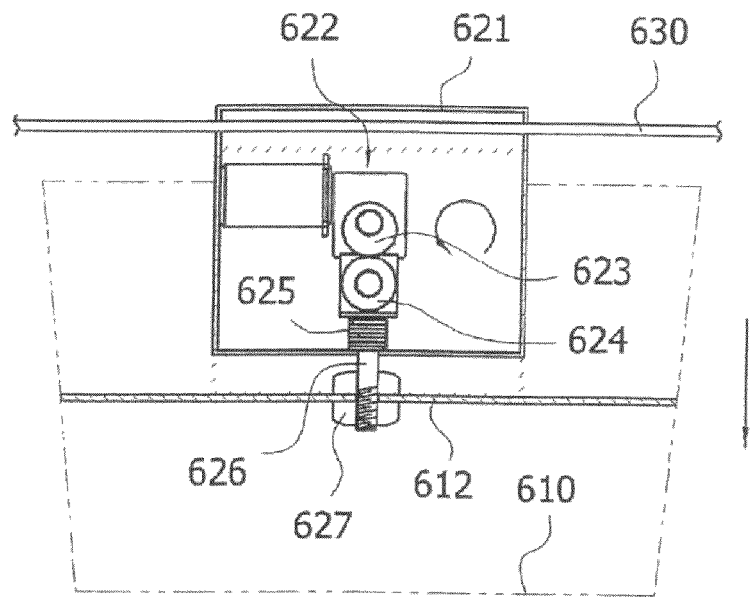

As shown in FIG. 1 and FIG. 2, the inside of the container part 1 of the cart, which has passed out the cart outside surface washing means 500, is washed by the cart inside space washing means 600. The cart inside space washing means 600 removes the dirt from the inside of the container part 1 of the cart by vibration of the brushes. FIG. 19 is a perspective view illustrating the cart inside space washing means 600 and FIGS. 20(*a*) and 20(*b*) are sectional views illustrating main part of the cart inside space washing means 600. As shown in FIGS. 20(*a*) and 20(*b*), the cart inside space washing means 600 includes a vibrating brush 610, a brush driving unit 620, a movable column 640, a vertically actuating cylinder 650, and a horizontally actuating cylinder 660.

The vibrating brush 610 has a body shape corresponding to the inside space of the container part 1 of the cart. The outer surface of the empty body is provided with a plurality of hair. The vibrating brush 610 vibrates in a vertical direction by a housing 621, which will be described later herein, and thus removes the direct from the inside of the container part 1 of the cart.

The brush driving unit 620 is a driving part for vibrating the vibrating brush 610 in a vertical direction. As shown in FIGS. 20(*a*) and 20(*b*), the brush driving unit 620 includes a housing 621, a decelerating motor 622 inside the housing 621, a driving cam 623, a driven cam 624, a rod 626, and a spring 625.

The decelerating motor 622 is fixed to the inside surface of the wall of the housing 621 and rotates the driving cam 623 connected to the decelerating motor 622. The driving cam 623 is an eccentric cam having an eccentric axis. A lower portion of the driving cam 623 is engaged with the driven cam 624 and linearly moves in a vertical direction by rotation of the driving cam 623. For the linear motion of the driven cam 624, the rod 626 is connected to a lower portion of the driven cam 624 and the spring 625 is wound around the outer surface of the rod 626. The rod 626 penetrates through a lower plate of the housing 621 and a barrier plate 612, which crosses the inside space of the vibrating brush 610 in a horizontal direction. An end of the rod 626 is provided with threads. An upper portion and a lower portion of the barrier plate 612 are engaged with fixing nuts 627 so that the rod 626 and the barrier plate 612 are combined with each other and can be moved as a single body.

With such a structure, as shown in FIGS. 20(*a*) and 20(*b*), when the driving cam 623 rotates, the driven cam 624 engaged with the outer surface of the driving cam 623 is pushed downward periodically. For this instance, as shown in FIG. 20(*b*), when the spring 625 contracts, the rod 626 moves downward. As the barrier plate 612 combined with the rod 626 is moved downward, the vibrating brush 610 is also moved downward. If the driving cam 623 rotates at very high speed, such operation is endlessly repeated and the vibrating brush 610 is moved very quickly in a vertical direction. That is, the vibrating brush 610 vibrates very quickly in the vertical direction.

After the vibrating brush 610 and the housing 621 are inserted into the cart, transported by the cart transporting means 200, and perform the washing process, they must be returned to the original positions for washing a next cart in the same manner. For this, a structure, which moves the vibrating brush 610 and the housing 621 in the vertical direction and the horizontal direction, is needed. As shown in FIG. 19, the cart inside space washing means 600 includes a movable column 640, a horizontal bar 630, a guide rail 670, a vertical cylinder 650, and a lateral cylinder 660.

The movable columns 640 are located at both sides of the cart transporting means 200 in a vertically erecting manner and support both the housing 621 and the vibrating brush 610. The movable columns 640 are structured to guide vertical motion and lateral motion of the vibrating brush 610 and the housing 621. That is, the horizontal bar 630 penetrates through an upper portion of the housing 621 and is connected to the movable columns 640. Ends of the horizontal bar 630 are provided with guide blocks 632. In addition, the outer surfaces of the guide blocks 632 are provided with two guide protrusions (not shown). The guide protrusions are inserted into the guide grooves 643 formed on inside surfaces of the movable columns 640 and structure to move in a vertical direction.

A lower portion of each of the guide blocks 632 is provided with a vertically actuating cylinder 650. An end of the vertically actuating cylinder 650 is fixed to the lower surface of the guide block 632, and a remaining end of the vertically actuating cylinder 650 is fixed to an associated movable column 640. As the vertically actuating cylinder 650 expands or contracts by air pressure, the guide block 632 is moved upwards or downwards in a vertical direction along the guide groove 642 of the movable column 640, so that the height of the vibrating brush 610 can be adjusted.

As mentioned above, the movable columns 640 are horizontally movable. For this, each of the movable columns 640 is provided with a horizontally actuating cylinder 660 which moves the movable column 640 in a horizontal direction in parallel with a moving direction of the cart as it contracts and expands by air pressure. An end of the horizontally actuating cylinder 660 is fixed to the movable column 649, a remaining end of the horizontally actuating cylinder 660 is fixed an inside surface of the wall of the housing, or a fixed structure (not shown). In order to guide the linear motion performed by the horizontally actuating cylinder 660, a guide piece 644 protrudes from a lower portion of the movable column 640. The guide piece 644 is structured to slide along the guide rail 670, which is fixed on the bottom of the housing.

Figure 21:
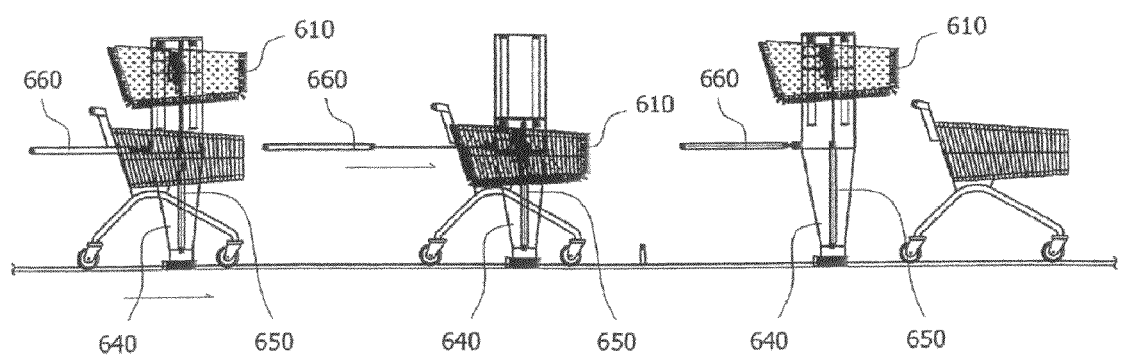
FIG. 21 is a side view illustrating operation in which the cart is washed by the cart inside space washing means.
Figure 22:
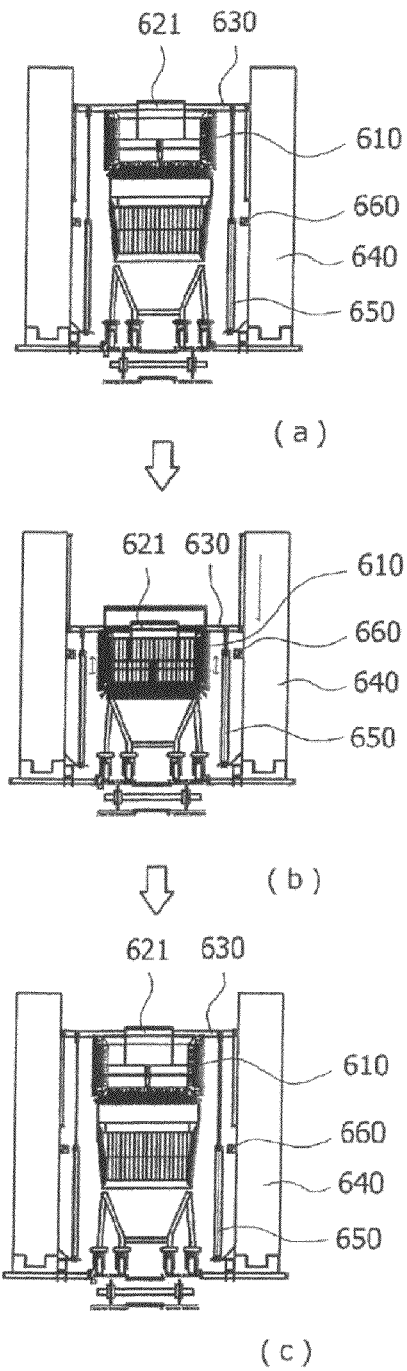
FIGS. 22(a), 22(b) and 22(c) are front views illustrating operation in which the cart is washed by the cart inside space washing means.

FIG. 21 and FIGS. 22(*a*), 22(*b*) and 22(*c*) are a side view and front views, respectively, illustrating operation that the cart inside space washing means 600 washes the cart.

As shown in FIG. 21 and FIGS. 22(*a*), 22(*b*) and 22(*c*), when the cart reaches the cart inside space washing means 600, the vertically actuating cylinder 650 contracts and is disposed inside the container part 1 of the cart. Next, the decelerating motor 622 starts to operate, and the vibrating brush 610 vibrates in the container part 1 of the cart and the washing is performed. Since the cart continuously progresses thanks to the cart transporting means 200, the vibrating brush 610 is moved along with the cart. As a result, the horizontally actuating cylinder 660 comes to expand and the movable columns 640 are moved horizontally along the guide rail 670.

After the inside of the cart has been washed, the vibrating brush 610 is returned to the original position and standby for washing of a next cart. For this, washing of the current cart is finished, the vertically actuating cylinder 650 expands and the vibrating brush 610 is lifted upwards and separated from the container part 1 of the cart. Next, the horizontally actuating cylinder 660 contracts, and the vibrating brush 610 is returned to its original position.

Timing adjustment of vibration operation of the vibrating brush 610, and contracting and expanding operations of the vertically actuating cylinder 650 and the horizontally actuating cylinder 660 is performed by a sensor (not shown) which detects positions of the casters 2 of the cart.

Figure 23:
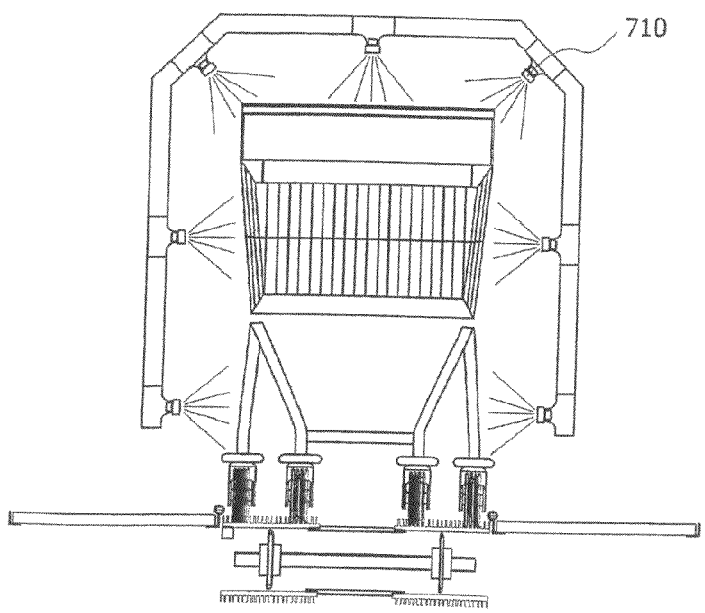
FIG. 23 is a front view illustrating a cart rinsing means.

After the inside of the cart is washed in the above-mentioned manner, as shown in FIG. 1 and FIG. 2, the cart is rinsed with clean water by the rinsing means 700 in order to completely remove the remaining dirt. FIG. 23 is a front view illustrating the rinsing means 700. As shown in FIG. 23, like the high pressure washing water spraying means 300, the rinsing means 700 includes a plurality of nozzles 710 and is structured to spray high pressure washing water. By the rinsing means 700. the dirt remaining on the cart after the washing can be completely removed.

As shown in FIG. 1 and FIG. 2, after the rinsing is finished by the rinsing means 700, water droplets on the surface of the can is removed by a drying means 800 in the cart drying unit. The drying means 800 is a blower, which blows dry hot air and completely removes the water droplets by blowing hot air to the surface of the cart.

As described above, as shown in FIG. 1 and FIG. 2, the cart, which has undergone sequentially the washing process and the drying process by the help of the cart transporting means 200, is discharged by the cart discharging unit.

Figure 24:
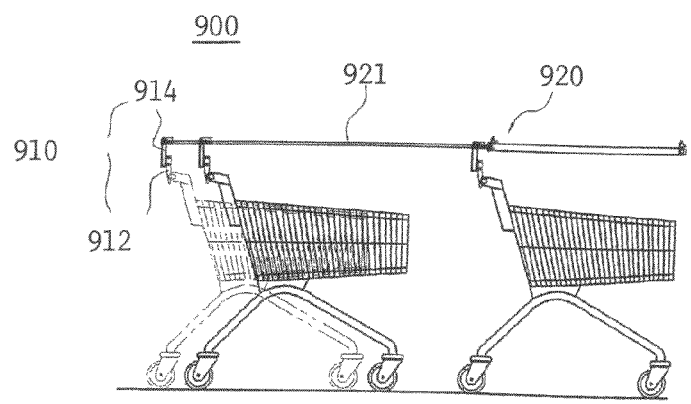
FIG. 24 is a view illustrating a method of discharging the cart from a cart discharging unit.

As shown in FIG. 1, the cart discharging unit includes a second inclined surface 20 and a cart discharging means 900, which are adjacent to an end stage of the cart drying unit. The carts are pulled by the cart discharging means 900 one by one and discharged along the second inclined surface 20. FIG. 24 schematically shows a cart discharging method in the cart discharging unit. The cart discharging means 900 includes a pushing member 910 and a second actuator 920.

The pushing member 910 pushes the handle 4 of the cart and discharges the cart outside the cart washing machine. ft is preferable that the pushing member 910 be structured to be rotatable in one direction like the pushing means 100 used in the cart loading unit. The pushing member 910 is reciprocated in a back-and-forth direction by the second actuator 920. After the second actuator 920 expands and thus it comes into contact with the back surface of the handle 4 of the cart, the second actuator 920 contracts. As a result, the pushing member 910 comes to push the handle 4 of the cart and the cart is discharged along the second inclined surface 20 to the outside of the can washing machine.

Figure 25:
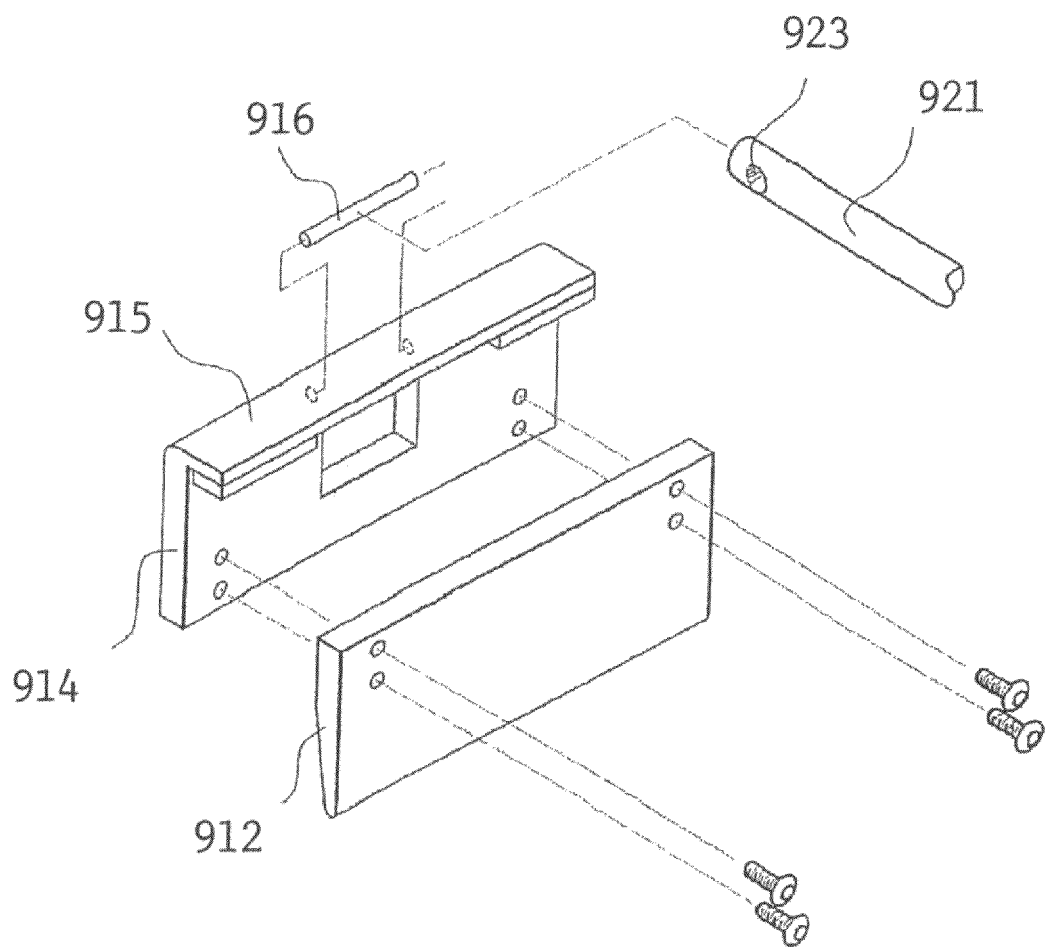
FIG. 25 is an exploded perspective view illustrating the detailed structure of a pushing member.

The pushing member 910 is structured to pivot in only one direction like the pushing means 100 of the cart loading unit. FIG. 25 is an exploded perspective view illustrating the overall structure of the pushing member 910. As shown in FIG. 25, the pushing member 910 includes a pushing plate 912 and a pivoting plate 914.

The pushing plate 912 is a plate member which comes into direct contact with the back surface of the handle 4 of the cart and thus pushes the cart forwards.

The pivoting plate 914 is a plate member which is moved by the connection to the second actuator 920 and which pivots the pushing plate 912 in one direction. As shown in FIG. 25, an upper portion of the pivoting plate 914 is bent in a horizontal direction and thus the pivoting plate 914 has a section in the reversed form of a letter "L." A lower portion of the bent portion 915 is cut and open. The horizontal shaft 916 is inserted into the opening of the cut portion 915. The horizontal shaft 916 is coupled to a cylinder rod 921 of the second pneumatic actuator. An end of the cylinder rod 921 is provided with an insertion hole 923 and the horizontal shaft 916 is inserted into the insertion hole 923.

Figure 26:
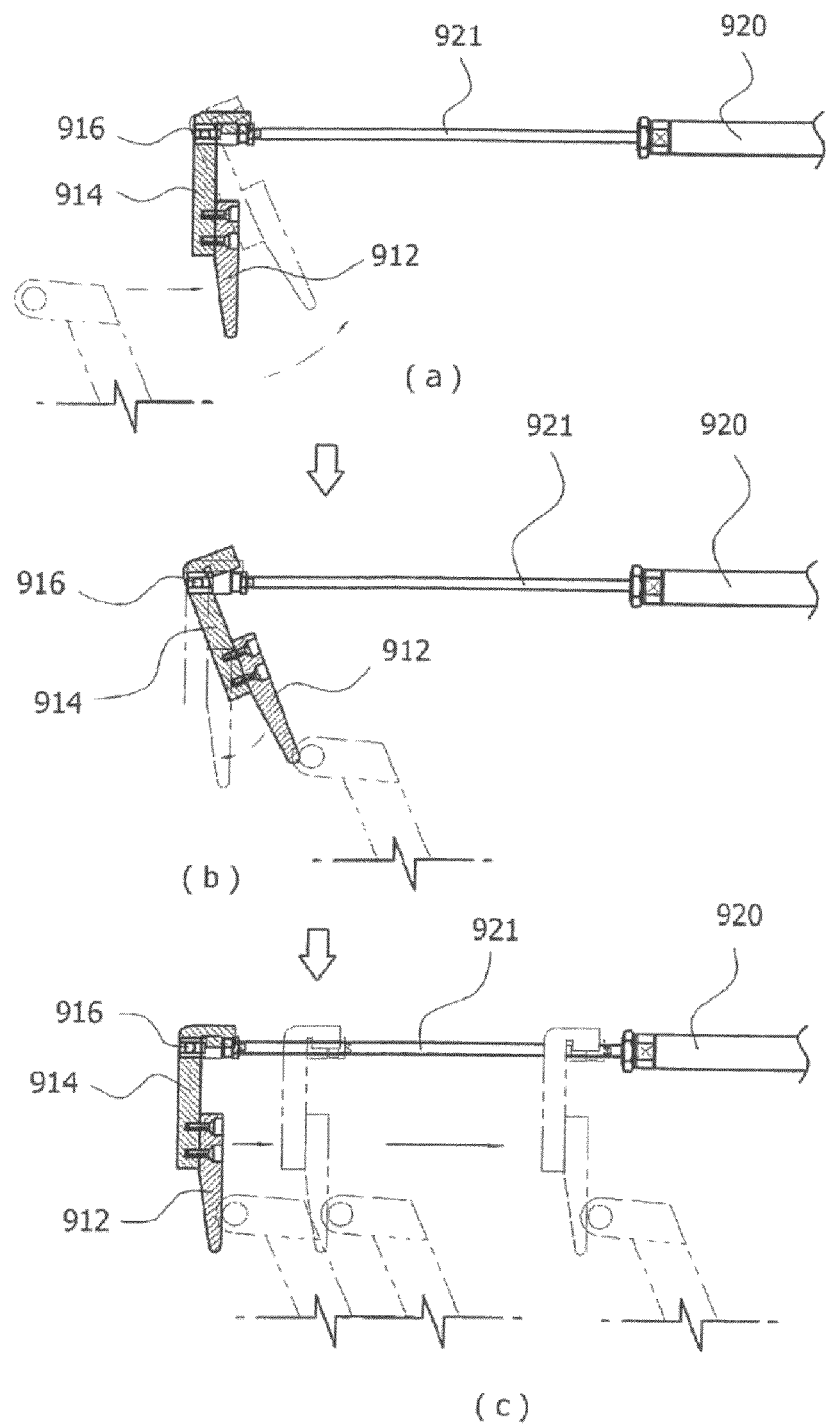
FIGS. 26(a), 26(b) and 26(c) are side views illustrating operation of the cart discharging means.

FIGS. 26(a) through 26(c) are side views illustrating operational relationship of elements of the cart discharging means 900 having the above-described structure. As shown in FIG. 26(a), the second actuator 920 is in an expanding state, and the cart progresses with the help of the cart transporting means 200. When the front surface of the handle 4 of the cart comes into contact with the pushing plate 912, the pivoting plate 914 relatively pivots about the horizontal shaft 916 serving as a pivoting point by the cylinder 921. As a result, the cart can progress without interference with the pushing plate 912. After the handle 4 of the cart passes by the pivoting plate 914, as shown in FIG. 26(b), the pivoting plate 914 is pivoted again and returned to the original position. Next, as shown in FIG. 26(c), the second actuator 920 contracts and thus the pushing plate 912 comes to push the back surface of the handle 4 of the cart. As a result, the cart is discharged along the second inclined surface 20. In the case in which the pivoting plate 914 pushes the handle 4 of the cart, the bent portion 915 is interrupted and supported by an end of the cylinder rod 921. As a result, it is possible to prevent the bent portion 915 from pivoting.

As described above, a plurality of discharged carts is temporarily stored in an overlapping manner and transported to shopping centers. As a result, it is possible to use clean shopping carts.

Although it is not shown, the shopping cart washing machine. is structured such that a water tank is installed at the downstream side of the cart transporting means, discharged washing water is temporarily stored in the water tank, a waste water treating device is provided inside the washing machine, the water collected in the water tank is purified, and some portion of the purified is reused and the remaining is discharged to a water source.

The invention is described in detail with reference to embodiments but the scope of the invention is not limited to the embodiments. The invention may include substantial equivalents of the embodiments.

The invention claimed is:

1. A shopping cart washing machine comprising:
   a cart transporting unit configured to transport a cart in a forward direction;
   a high pressure washing water spraying unit configured to wash the cart by spraying high pressure washing water to a surface of the cart;
   a handle washing unit configured to wash a handle of the cart by brushing an upper surface and a lower surface, of the handle of the cart;
   a cart outside surface washing unit configured to wash an outside surface of a container part of the cart by brushing sides of the container part;
   a cart inside space washing unit configured to remove dirt from the container part by vertical vibrations;
   a rinsing unit configured to remove dirt remaining on the surface of the washed cart by spraying high pressure washing water; and
   a drying unit configured to remove water droplets remaining on the surface of the washed cart using hot air.

2. The shopping cart washing machine according to claim 1, wherein the cart transporting unit includes:
   a pair of left and right chains, each engaged with sprockets;
   a pair of upper plates coupled to upper portions of the chains for supporting left and right casters of the cart, respectively, and moving along the chains for transporting the cart in a horizontal direction;
   an anti-shaking member coupled to the left and right chains the anti-shaking member being disposed to cross a gap between the left and right chains and to protrude from upper surfaces of the upper plates; and a horizontal bar of the cart placed on the anti-shaking member, the horizontal bar being configured to prevent the cart from shaking.

3. The shopping cart washing machine according to claim 2, wherein the anti-shaking member includes:
  a horizontal fixed shaft fixed to sides of the left and right chains at ends thereof, respectively; and
  a fixing member extending from an upper surface of the horizontal fixed shaft for transporting the cart without shaking by holding the horizontal bar of the cart, the fixing member having a recess at a center portion thereof for receiving the horizontal bar of the cart therein so that the cart does not shake.

4. The shopping cart washing machine according to claim 1, wherein the high pressure washing water spraying unit includes:
  a washing water pipe having a tunnel shape through which high pressure washing water passes; and
  a plurality of rotating nozzles configured to spray the high pressure washing water by rotating themselves at regular intervals in the washing water pipe.

5. The shopping cart washing machine according to claim 1, wherein the handle washing unit includes:
  a first horizontal brush and a second horizontal brush arranged adjacent to one another in a vertical direction, the first horizontal brush and the second horizontal brush being configured to brush an upper surface and a lower surface of the handle of the cart, respectively;
  a brush arm supporting the first horizontal brush and the second horizontal brush in a rotatable manner while the brush arm is in a close contact with the first horizontal brush and the second horizontal brush, the brush arm having a guide protrusion at each side thereof;
  a first actuator actuating the brush arm and the first horizontal brush and the second horizontal brush supported by the brush arm in a back-and-forth direction; and
  a guide rail guiding the guide protrusions of the brush arm.

6. The shopping cart washing machine according to claim 1, wherein the cart outside surface washing unit includes:
  a first vertical brush and a second vertical brush, erecting at both sides of the cart and rotating to brush side surfaces of the container part of the cart,
  wherein a shaft of the first vertical brush is coupled to a first upper bracket at an upper portion and to a first lower bracket at a lower portion in a rotatable manner,
  wherein a shaft of the second vertical brush is coupled to a second upper bracket at an upper portion and to a second lower bracket at a lower portion in a rotatable manner,
  wherein the first upper bracket and the first lower bracket are fixedly coupled to a first rotational shaft rotatably installed on a bottom of the cart transporting unit, and the second upper bracket and the second lower bracket are fixedly coupled to a second rotational shaft rotatably installed on the bottom of the cart transporting unit
  wherein the first rotational shaft and the second rotational shaft are provided with a first tension spring and a second tension spring, respectively so that the first vertical brush and the second vertical brush are returned to their original positions after washing the outside surface of the container part of the cart.

7. The shopping cart washing machine according to claim 1, wherein the cart inside space washing unit includes:
  a vibrating brush having a body and a plurality of brush hair attached to an outer surface of the body, the vibrating brush removing the dirt in the container part of the cart by vertically vibrating; and
  a brush driving unit coupled to an upper portion of the vibrating brush and vibrating the vibrating brush in a vertical direction.

8. The shopping cart washing machine according to claim 7, wherein the brush driving unit is coupled to a horizontal bar,
  wherein a vertically actuating cylinder provided to a lower end portion of the horizontal bar, the vertically actuating cylinder actuating the vibrating brush and the brush driving unit by moving the horizontal bar in a vertical direction,
  wherein movable columns are installed at both sides of the horizontal bar for guiding the horizontal bar in a vertical direction and reciprocate in a cart transporting direction, and
  wherein column moving cylinders are provided at the back of the columns for reciprocating the columns.

9. The shopping cart washing machine according to claim 7, wherein the brush driving unit includes:
  a housing;
  a decelerating motor fixed to an inside surface of the housing;
  a driving cam eccentrically rotating by the decelerating motor;
  a driven cam located under the driving cam and linearly moving in a vertical direction by rotation of the driving cam;
  a rod extending downwards from a lower portion of the driven cam; and
  a spring provided to surround an outer surface of the rod,
  wherein the rod sequentially penetrates a lower plate of the housing and a barrier plate, and
  wherein fixing nuts are coupled to an upper portion and a lower portion, of the barrier plate for coupling the rod and the barrier plate to one another.

10. The shopping cart washing machine according to claim 1, further comprising:
  a cart loading unit located near a starting stage of the cart transporting unit, the cart loading unit being configured to push the cart for washing,
  wherein the cart loading unit includes:
    a first inclined surface extending from a ground surface to the starting stage of the cart transporting unit; and
    a pushing unit configured to push the cart so that the cart can move along the first inclined surface.

11. The shopping cart washing machine according to claim 10, wherein the pushing unit includes:
  a pair of left and right chains, each engaged with a first sprocket and a second sprocket and moving in a circulating manner;
  a decelerating motor connected to the first sprocket; and
  a pushing plate coupled to and disposed between the left and right chains for pushing the handle of the cart.

12. The shopping cart washing machine according to claim 11, wherein the pushing unit further includes:
  a first fixed shaft arranged to be fixed to the left and right chains at both ends thereof, the first fixed shaft being inserted into a hole of a first hollow member, wherein a lower end portion of the first hollow member is provided with a fixing block and the pushing plate is coupled and fixed to a front portion of the fixing block by nuts and bolts, and
  a second fixed shaft disposed at downstream side of the first fixed shaft in parallel with the first fixed shaft and fixed to the chains, the second fixed shaft being configured to prevent the pushing plate from pivoting in a backward direction.

13. The shopping cart washing machine according to claim 10, wherein the first inclined surface is provided with an anti-slipping unit which prevents the cart from slipping down on the first inclined surface.

14. The shopping cart washing machine according to claim 13, wherein the anti-slipping unit includes:
   a supporting plate configured to support a back of the horizontal bar of the cart;
   a pivoting member supporting the supporting plate in a manner such that the supporting plate pivots only in a forward direction;
   a supporting block configured to prevent the pivoting member from pivoting in a backward direction; and
   a twisting spring for giving elastic force to the pivoting member so that the pivoting member is returned to its original position after pivoting in the forward direction.

15. The shopping cart washing machine according to claim 1, further comprising:
   a cart discharging unit configured to discharge the washed cart and provided at an end stage of the cart transporting unit,
   wherein the cart discharging unit includes:
      a second inclined surface extending from the end stage of the cart transporting unit to a ground surface; and
      a cart discharging unit configured to push the cart such that the cart moves along the second inclined surface and is discharged outside the shopping cart washing machine.

16. The shopping cart washing machine according to claim 15, wherein the cart discharging unit includes:
   a pushing member (910) configured to push the handle of the cart; and
   a second actuator actuating the pushing member in a back-and-forth direction.

17. The shopping cart washing machine according to claim 16, wherein the pushing member includes:
   a pushing plate for pushing the back surface of the handle of the cart; and
   a pivoting plate connected to the second actuator, the pivoting plate being configured to move and pivot the pushing plate in one direction.

* * * * *